United States Patent
Lee et al.

(10) Patent No.: US 9,556,443 B2
(45) Date of Patent: Jan. 31, 2017

(54) YEAST CELL WITH INACTIVATED NADH DEHYDROGENASE AND METHOD OF PRODUCING LACTATE USING THE YEAST CELL

(71) Applicant: Samsung Electronics Co., Ltd., Suwon-si, Gyeonggi-do (KR)

(72) Inventors: Ju Young Lee, Daegu (KR); Chang Duk Kang, Gwacheon-si (KR); Jin Kyu Kang, Daegu (KR); Seung Hyun Lee, Asan-si (KR); Kwang Myung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 140 days.

(21) Appl. No.: 14/335,728

(22) Filed: Jul. 18, 2014

(65) Prior Publication Data
US 2015/0024444 A1 Jan. 22, 2015

(30) Foreign Application Priority Data
Jul. 19, 2013 (KR) .................. 10-2013-0085520

(51) Int. Cl.
*C12N 15/81* (2006.01)
*C12P 7/56* (2006.01)
*C12N 9/02* (2006.01)

(52) U.S. Cl.
CPC ............. *C12N 15/81* (2013.01); *C12N 9/0036* (2013.01); *C12P 7/56* (2013.01); *Y02P 20/52* (2015.11)

(58) Field of Classification Search
None
See application file for complete search history.

(56) References Cited

U.S. PATENT DOCUMENTS

2005/0148055 A1 7/2005 Walther et al.

FOREIGN PATENT DOCUMENTS

| JP | 2004-024140 B2 | 1/2004 |
| KR | 2009-0008446 A | 1/2009 |
| KR | 2010-0012986 A | 2/2010 |
| WO | WO 2004/099425 A2 | 11/2004 |
| WO | WO 2012/074818 A2 | 6/2012 |
| WO | WO 2012/177726 A1 | 12/2012 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Hacioglu et al., "Identification of respiratory chain gene mutations that shorten replicative life span in yeast", *Experimental Gerontology*, 47:149-153 (2012).
Sauer et al., "16 years research on lactic acid production with yeast-ready for the market?", *Biotechnology and Genetic Engineering Reviews*, 27: 229-256 (2010).
Tokuhiro et al., Double mutation of the PDC1 and ADH1 improves lactate production in the yeast *Saccharomyces cerevisiae* expressing the bovine lactate dehydrogenase gene, *Applied Genetics and Molecular Biotechnology*, 82: 883-890 (2009).
European Patent Office, Extended European Search Report in Application No. 14177896.9 dated Dec. 1, 2014.

* cited by examiner

*Primary Examiner* — Christian Fronda
(74) *Attorney, Agent, or Firm* — Leydig, Voit & Mayer, Ltd.

(57) ABSTRACT

Provided are a yeast cell in which the activity of an external mitochondrial NADH dehydrogenase is decreased and a method of producing lactate by using the yeast cell.

14 Claims, 8 Drawing Sheets

SEQUENCE LISTING

```
<160> NUMBER OF SEQ ID NOS: 55

<210> SEQ ID NO 1
<211> LENGTH: 560
<212> TYPE: PRT
<213> ORGANISM: Saccharomyces cerevisiae
```

<400> SEQUENCE: 1

Met Ile Arg Gln Ser Leu Met Lys Thr Val Trp Ala Asn Ser Ser Arg
1               5                   10                  15

Phe Ser Leu Gln Ser Lys Ser Gly Leu Val Lys Tyr Ala Lys Asn Arg
            20                  25                  30

Ser Phe His Ala Ala Arg Asn Leu Leu Glu Asp Lys Lys Val Ile Leu
        35                  40                  45

Gln Lys Val Ala Pro Thr Thr Gly Val Val Ala Lys Gln Ser Phe Phe
    50                  55                  60

Lys Arg Thr Gly Lys Phe Thr Leu Lys Ala Leu Leu Tyr Ser Ala Leu
65                  70                  75                  80

Ala Gly Thr Ala Tyr Val Ser Tyr Ser Leu Tyr Arg Glu Ala Asn Pro
                85                  90                  95

Ser Thr Gln Val Pro Gln Ser Asp Thr Phe Pro Asn Gly Ser Lys Arg
            100                 105                 110

Lys Thr Leu Val Ile Leu Gly Ser Gly Trp Gly Ser Val Ser Leu Leu
        115                 120                 125

Lys Asn Leu Asp Thr Thr Leu Tyr Asn Val Val Val Val Ser Pro Arg
    130                 135                 140

Asn Tyr Phe Leu Phe Thr Pro Leu Leu Pro Ser Thr Pro Val Gly Thr
145                 150                 155                 160

Ile Glu Leu Lys Ser Ile Val Glu Pro Val Arg Thr Ile Ala Arg Arg
                165                 170                 175

Ser His Gly Glu Val His Tyr Tyr Glu Ala Glu Ala Tyr Asp Val Asp
            180                 185                 190

Pro Glu Asn Lys Thr Ile Lys Val Lys Ser Ser Ala Lys Asn Asn Asp
        195                 200                 205

Tyr Asp Leu Asp Leu Lys Tyr Asp Tyr Leu Val Gly Val Gly Ala
    210                 215                 220

Gln Pro Asn Thr Phe Gly Thr Pro Gly Val Tyr Glu Tyr Ser Ser Phe
225                 230                 235                 240

Leu Lys Glu Ile Ser Asp Ala Gln Glu Ile Arg Leu Lys Ile Met Ser
                245                 250                 255

Ser Ile Glu Lys Ala Ala Ser Leu Ser Pro Lys Asp Pro Glu Arg Ala
            260                 265                 270

Arg Leu Leu Ser Phe Val Val Gly Gly Pro Thr Gly Val Glu
        275                 280                 285

Phe Ala Ala Glu Leu Arg Asp Tyr Val Asp Gln Asp Leu Arg Lys Trp
    290                 295                 300

Met Pro Glu Leu Ser Lys Glu Ile Lys Val Thr Leu Val Glu Ala Leu
305                 310                 315                 320

Pro Asn Ile Leu Asn Met Phe Asp Lys Tyr Leu Val Asp Tyr Ala Gln
                325                 330                 335

Asp Leu Phe Lys Glu Glu Lys Ile Asp Leu Arg Leu Lys Thr Met Val
            340                 345                 350

Lys Lys Val Asp Ala Thr Thr Ile Thr Ala Lys Thr Gly Asp Gly Asp
        355                 360                 365

Ile Glu Asn Ile Pro Tyr Gly Val Leu Val Trp Ala Thr Gly Asn Ala
    370                 375                 380

Pro Arg Glu Val Ser Lys Asn Leu Met Thr Leu Glu Glu Gln Asp
385                 390                 395                 400

Ser Arg Arg Gly Leu Leu Ile Asp Asn Lys Leu Gln Leu Leu Gly Ala
                405                 410                 415

-continued

```
Lys Gly Ser Ile Phe Ala Ile Gly Asp Cys Thr Phe His Pro Gly Leu
            420                 425                 430

Phe Pro Thr Ala Gln Val Ala His Gln Glu Gly Glu Tyr Leu Ala Gln
            435                 440                 445

Tyr Phe Lys Lys Ala Tyr Lys Ile Asp Gln Leu Asn Trp Lys Met Thr
450                 455                 460

His Ala Lys Asp Asp Ser Glu Val Ala Arg Leu Lys Asn Gln Ile Val
465                 470                 475                 480

Lys Thr Gln Ser Gln Ile Glu Asp Phe Lys Tyr Asn His Lys Gly Ala
                485                 490                 495

Leu Ala Tyr Ile Gly Ser Asp Lys Ala Ile Ala Asp Leu Ala Val Gly
            500                 505                 510

Glu Ala Lys Tyr Arg Leu Ala Gly Ser Phe Thr Phe Leu Phe Trp Lys
            515                 520                 525

Ser Ala Tyr Leu Ala Met Cys Leu Ser Phe Arg Asn Arg Val Leu Val
            530                 535                 540

Ala Met Asp Trp Ala Lys Val Tyr Phe Leu Gly Arg Asp Ser Ser Ile
545                 550                 555                 560

<210> SEQ ID NO 2
<211> LENGTH: 545
<212> TYPE: PRT
<213> ORGANISM: Saccharomyces cerevisiae

<400> SEQUENCE: 2

Met Leu Pro Arg Leu Gly Phe Ala Arg Thr Ala Arg Ser Ile His Arg
1               5                   10                  15

Phe Lys Met Thr Gln Ile Ser Lys Pro Phe His Ser Thr Glu Val
            20                  25                  30

Gly Lys Pro Gly Pro Gln Gln Lys Leu Ser Lys Ser Tyr Thr Ala Val
            35                  40                  45

Phe Lys Lys Trp Phe Val Arg Gly Leu Lys Leu Thr Phe Tyr Thr Thr
    50                  55                  60

Leu Ala Gly Thr Leu Tyr Val Ser Tyr Glu Leu Tyr Lys Glu Ser Asn
65                  70                  75                  80

Pro Pro Lys Gln Val Pro Gln Ser Thr Ala Phe Ala Asn Gly Leu Lys
                85                  90                  95

Lys Lys Glu Leu Val Ile Leu Gly Thr Gly Trp Gly Ala Ile Ser Leu
            100                 105                 110

Leu Lys Lys Leu Asp Thr Ser Leu Tyr Asn Val Thr Val Val Ser Pro
            115                 120                 125

Arg Ser Phe Phe Leu Phe Thr Pro Leu Leu Pro Ser Thr Pro Val Gly
    130                 135                 140

Thr Ile Glu Met Lys Ser Ile Val Glu Pro Val Arg Ser Ile Ala Arg
145                 150                 155                 160

Arg Thr Pro Gly Glu Val His Tyr Ile Glu Ala Glu Ala Leu Asp Val
                165                 170                 175

Asp Pro Lys Ala Lys Lys Val Met Val Gln Ser Val Ser Glu Asp Glu
            180                 185                 190

Tyr Phe Val Ser Ser Leu Ser Tyr Asp Tyr Leu Val Ser Val Gly
            195                 200                 205

Ala Lys Thr Thr Thr Phe Asn Ile Pro Gly Val Tyr Gly Asn Ala Asn
    210                 215                 220

Phe Leu Lys Glu Ile Glu Asp Ala Gln Asn Ile Arg Met Lys Leu Met
```

```
                225                 230                 235                 240
Lys Thr Ile Glu Gln Ala Ser Ser Phe Pro Val Asn Asp Pro Glu Arg
                    245                 250                 255
Lys Arg Leu Leu Thr Phe Val Val Gly Gly Gly Pro Thr Gly Val
                260                 265                 270
Glu Phe Ala Ala Glu Leu Gln Asp Tyr Ile Asn Gln Asp Leu Arg Lys
                275                 280                 285
Trp Met Pro Asp Leu Ser Lys Glu Met Lys Val Ile Leu Ile Glu Ala
                290                 295                 300
Leu Pro Asn Ile Leu Asn Met Phe Asp Lys Thr Leu Ile Lys Tyr Ala
305                 310                 315                 320
Glu Asp Leu Phe Ala Arg Asp Glu Ile Asp Leu Gln Val Asn Thr Ala
                    325                 330                 335
Val Lys Val Val Glu Pro Thr Tyr Ile Arg Thr Leu Gln Asn Gly Gln
                340                 345                 350
Thr Asn Thr Asp Ile Glu Tyr Gly Met Leu Val Trp Ala Thr Gly Asn
                355                 360                 365
Glu Pro Ile Asp Phe Ser Lys Thr Leu Met Ser Arg Ile Pro Glu Gln
                370                 375                 380
Thr Asn Arg Arg Gly Leu Leu Ile Asn Asp Lys Leu Glu Leu Leu Gly
385                 390                 395                 400
Ser Glu Asn Ser Ile Tyr Ala Ile Gly Asp Cys Thr Ala His Thr Gly
                    405                 410                 415
Phe Phe Pro Thr Ala Gln Val Ala His Gln Glu Gly Glu Tyr Leu Ala
                420                 425                 430
Lys Ile Leu Asp Lys Lys Leu Gln Ile Glu Gln Leu Glu Trp Asp Met
                435                 440                 445
Leu Asn Ser Thr Asp Glu Thr Glu Val Ser Arg Leu Gln Lys Glu Val
                450                 455                 460
Asn Leu Arg Lys Ser Lys Leu Asp Lys Phe Asn Tyr Lys His Met Gly
465                 470                 475                 480
Ala Leu Ala Tyr Ile Gly Ser Glu Thr Ala Ile Ala Asp Leu His Met
                    485                 490                 495
Gly Asp Ser Ser Tyr Gln Leu Lys Gly Met Phe Ala Phe Leu Phe Trp
                500                 505                 510
Lys Ser Ala Tyr Leu Ala Met Cys Leu Ser Ile Arg Asn Arg Ile Leu
                515                 520                 525
Ile Ala Met Asp Trp Thr Lys Val Tyr Phe Leu Gly Arg Asp Ser Ser
                530                 535                 540
Val
545

<210> SEQ ID NO 3
<211> LENGTH: 1683
<212> TYPE: DNA
<213> ORGANISM: Saccharomyces cerevisiae

<400> SEQUENCE: 3
atgattagac aatcattaat gaaaacagtg tgggctaact cctccaggtt tagcctacag      60
agcaagtcgg ggcttgtgaa atatgccaaa aatagatcgt tccatgcagc aagaaatttg     120
ctagaggaca agaaagtcat tttgcaaaaa gtggcgccca ctactggcgt tgttgcgaag     180
cagtcctttt tcaagagaac tgggaaattt actttgaagg ctttattgta ttctgccctc     240
gcgggtacgg cttacgtttc atactcactt taccgagaag ctaacccttc tacccaagtt     300
```

-continued

```
cctcaatcgg acactttttcc aaacggttca agaggaaga ctttggtaat tctgggctcc      360
ggttggggtt ctgtgtcgct tttgaaaaat ttggacacca cgttgtataa tgttgttgtt      420
gtttctccaa gaaattattt tcttttact ccgctattgc catctacccc agttggtacc       480
atcgaattga aatctattgt tgaacctgtc aggactattg ctagaagatc gcacggtgaa      540
gtccattact atgaagctga agcgtacgac gttgatcctg aaaacaaaac aattaaggtc      600
aaatcttccg ctaagaataa cgactacgac ttggacttga aatacgacta tctggttgtc      660
ggtgtgggtg ctcaaccaaa cactttggt actccgggag tttatgaata ttcttctttc       720
ttgaaggaaa tatccgacgc tcaagagatc agattaaaaa ttatgtccag tattgagaaa      780
gctgcctccc tatctccaaa agatcctgag agagcaagat tgttgagctt tgttgtcgtt     840
ggtggtggtc ccaccggtgt cgaatttgcc gctgaattga gagattatgt tgaccaggac      900
ttgagaaaat ggatgcccga attgagtaaa gaaattaaag tcactttggt ggaggctttg     960
ccaaacattt tgaacatgtt tgacaagtat ctcgttgact atgctcaaga tttattcaaa      1020
gaggaaaaaa tcgatttaag attgaaaaca atggttaaga aagttgacgc taccactata      1080
actgccaaaa ctggcgatgg tgacattgaa aatataccgt atggtgtatt agtttgggct      1140
acaggtaatg cgccaagaga agtgtctaag aacctaatga ctaaattaga ggaacaggac      1200
tcaagacgtg gtttgttgat agataacaaa cttcaacttt tgggtgctaa gggatctatt     1260
tttgctatcg gcgattgtac cttccaccct ggcttgttcc ctaccgctca agttgcccac     1320
caagaaggtg aatacttggc tcagtatttc aagaaagctt ataaaatcga tcaattgaac     1380
tggaaaatga cccatgctaa agacgattca gaagtcgcta gattaaagaa ccaaatagtc    1440
aaaacgcaat cgcaaattga agacttcaag tacaaccata agggtgctct ggcttatatt     1500
ggttcagata aagccattgc tgatcttgcc gttggtgaag ccaaatatag gttagccggc     1560
tcattcacct tcctattctg gaaatctgct tatttggcaa tgtgtctatc ctttagaaac    1620
agagttcttg tcgctatgga ttgggctaaa gtttatttct gggtagaga ttcatctatc     1680
tag                                                                   1683
```

```
<210> SEQ ID NO 4
<211> LENGTH: 1638
<212> TYPE: DNA
<213> ORGANISM: Saccharomyces cerevisiae

<400> SEQUENCE: 4
```

```
atgctgccca gacttggttt tgcgaggact gctaggtcca tacaccgttt caagatgacc       60
cagatctcta aaccttttt ccattccact gaagttggta agcccggacc acagcagaag      120
ctatcgaaat cttacactgc ggtattcaag aaatggtttg tcagaggttt aaagttaacc      180
ttttacacga cgttggccgg cacattgtat gtgtcatacg agctgtacaa agaatcgaac      240
ccacccaaac aggttcccca atcgaccgct tttgctaatg tttgaaaaa gaaggagctg       300
gttattttgg gtacaggctg gggcgccata tctcttttga agaaattaga cacgtctttg     360
tataacgtga ccgtggtgtc gccaagaagc ttctttttgt tcacaccgtt attaccctca      420
acgcctgtgg gtacgataga gatgaagtct attgtcgaac cggttagatc gatcgctaga      480
agaacgcctg gagaagttca ctacattgag gcggaagcgt ggacgttga tccaaaggcc     540
aaaaaagtaa tggtgcaatc ggtgtcagag gacgaatatt tcgtttcgag cttaagttac      600
gattatcttg ttgttagtgt aggcgctaaa accactactt ttaacattcc cggggtctat      660
```

```
ggcaatgcta acttcttgaa agagattgaa gatgctcaaa atattcgtat gaagttaatg      720
aaaaccatag aacaggcaag ttcatttcct gtgaacgatc cggaaaggaa gcgattatta      780
acgttcgtgg ttgttggagg gggccctacg ggggttgaat ttgccgccga actgcaagat      840
tacatcaatc aagatttgag gaagtggatg cccgacttaa gtaaagaaat gaaggttatc      900
ttaattgaag ccctgcctaa tatcctaaac atgttcgata agacgttgat caagtatgcc      960
gaggaccttt tgccagaga tgaaattgac ttgcaagtga atactgccgt gaaagtcgta      1020
gagccaacct atatacgcac tctgcaaaac ggccaaacaa acacggatat cgaatacggg      1080
atgctggttt gggccacggg aaatgaacca atcgatttt caaagacact gatgagtaga      1140
ataccggagc aaactaatag gcgtggtctg ttaattaatg acaagttgga gcttctcggt      1200
tctgagaatt cgatttatgc aattggtgat tgtaccgcac acacgggttt ctttcccacg      1260
gcacaagttg cacatcagga aggcgaatac ttggccaaga tcttggataa aaaattacag      1320
atagaacaat tggaatggga catgctcaac agtaccgatg aaactgaggt atcacgtcta      1380
caaaaagagg ttaatttgag gaaatctaag ttggataagt tcaactacaa gcatatgggt      1440
gcccttgcgt acatcggctc tgaaaccgca attgcagatt tgcatatggg cgactcatca      1500
taccagttga aaggtatgtt tgccttcttg ttttggaaat ccgcttattt ggccatgtgt      1560
ctctctatca ggaataggat tttaattgcc atggactgga ccaaagttta ctttcttgga      1620
agggattcct ccgtgtag                                                    1638

<210> SEQ ID NO 5
<211> LENGTH: 563
<212> TYPE: PRT
<213> ORGANISM: Saccharomyces cerevisiae

<400> SEQUENCE: 5

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
```

```
                195                 200                 205
Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln

<210> SEQ ID NO 6
<211> LENGTH: 591
<212> TYPE: PRT
<213> ORGANISM: Saccharomyces cerevisiae

<400> SEQUENCE: 6

Met Leu Lys Tyr Lys Pro Leu Leu Lys Ile Ser Lys Asn Cys Glu Ala
```

-continued

```
1               5                   10                  15
Ala Ile Leu Arg Ala Ser Lys Thr Arg Leu Asn Thr Ile Arg Ala Tyr
            20                  25                  30
Gly Ser Thr Val Pro Lys Ser Lys Ser Phe Glu Gln Asp Ser Arg Lys
            35                  40                  45
Arg Thr Gln Ser Trp Thr Ala Leu Arg Val Gly Ala Ile Leu Ala Ala
 50                  55                  60
Thr Ser Ser Val Ala Tyr Leu Asn Trp His Asn Gly Gln Ile Asp Asn
 65                  70                  75                  80
Glu Pro Lys Leu Asp Met Asn Lys Gln Lys Ile Ser Pro Ala Glu Val
                    85                  90                  95
Ala Lys His Asn Lys Pro Asp Asp Cys Trp Val Val Ile Asn Gly Tyr
                100                 105                 110
Val Tyr Asp Leu Thr Arg Phe Leu Pro Asn His Pro Gly Gly Gln Asp
                115                 120                 125
Val Ile Lys Phe Asn Ala Gly Lys Asp Val Thr Ala Ile Phe Glu Pro
            130                 135                 140
Leu His Ala Pro Asn Val Ile Asp Lys Tyr Ile Ala Pro Glu Lys Lys
145                 150                 155                 160
Leu Gly Pro Leu Gln Gly Ser Met Pro Pro Glu Leu Val Cys Pro Pro
                    165                 170                 175
Tyr Ala Pro Gly Glu Thr Lys Glu Asp Ile Ala Arg Lys Glu Gln Leu
                180                 185                 190
Lys Ser Leu Leu Pro Pro Leu Asp Asn Ile Ile Asn Leu Tyr Asp Phe
            195                 200                 205
Glu Tyr Leu Ala Ser Gln Thr Leu Thr Lys Gln Ala Trp Ala Tyr Tyr
    210                 215                 220
Ser Ser Gly Ala Asn Asp Glu Val Thr His Arg Glu Asn His Asn Ala
225                 230                 235                 240
Tyr His Arg Ile Phe Phe Lys Pro Lys Ile Leu Val Asp Val Arg Lys
                245                 250                 255
Val Asp Ile Ser Thr Asp Met Leu Gly Ser His Val Asp Val Pro Phe
                260                 265                 270
Tyr Val Ser Ala Thr Ala Leu Cys Lys Leu Gly Asn Pro Leu Glu Gly
            275                 280                 285
Glu Lys Asp Val Ala Arg Gly Cys Gly Gln Gly Val Thr Lys Val Pro
    290                 295                 300
Gln Met Ile Ser Thr Leu Ala Ser Cys Ser Pro Glu Glu Ile Ile Glu
305                 310                 315                 320
Ala Ala Pro Ser Asp Lys Gln Ile Gln Trp Tyr Gln Leu Tyr Val Asn
                325                 330                 335
Ser Asp Arg Lys Ile Thr Asp Asp Leu Val Lys Asn Val Glu Lys Leu
                340                 345                 350
Gly Val Lys Ala Leu Phe Val Thr Val Asp Ala Pro Ser Leu Gly Gln
            355                 360                 365
Arg Glu Lys Asp Met Lys Leu Lys Phe Ser Asn Thr Lys Ala Gly Pro
370                 375                 380
Lys Ala Met Lys Lys Thr Asn Val Glu Glu Ser Gln Gly Ala Ser Arg
385                 390                 395                 400
Ala Leu Ser Lys Phe Ile Asp Pro Ser Leu Thr Trp Lys Asp Ile Glu
                405                 410                 415
Glu Leu Lys Lys Lys Thr Lys Leu Pro Ile Val Ile Lys Gly Val Gln
            420                 425                 430
```

Arg Thr Glu Asp Val Ile Lys Ala Ala Glu Ile Gly Val Ser Gly Val
            435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Val Arg Arg Gly Thr
                485                 490                 495

Asp Val Leu Lys Ala Leu Cys Leu Gly Ala Lys Gly Val Gly Leu Gly
                500                 505                 510

Arg Pro Phe Leu Tyr Ala Asn Ser Cys Tyr Gly Arg Asn Gly Val Glu
                515                 520                 525

Lys Ala Ile Glu Ile Leu Arg Asp Glu Ile Glu Met Ser Met Arg Leu
                530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
                580                 585                 590

<210> SEQ ID NO 7
<211> LENGTH: 391
<212> TYPE: PRT
<213> ORGANISM: Saccharomyces cerevisiae

<400> SEQUENCE: 7

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
                20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg

```
                210               215                 220
Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
        290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
        370                 375                 380

Glu Leu Asp Leu His Glu Asp
385                 390

<210> SEQ ID NO 8
<211> LENGTH: 1692
<212> TYPE: DNA
<213> ORGANISM: Saccharomyces cerevisiae

<400> SEQUENCE: 8
atgtctgaaa ttactttggg taaatatttg ttcgaaagat taaagcaagt caacgttaac      60
accgttttcg gtttgccagg tgacttcaac ttgtccttgt ggacaagat  ctacgaagtt     120 gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctctgctca agctaagcaa ttgttgttgc accacacctt gggtaacggt     360
gacttcactg tttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact tgaacgtccc agctaagttg     540
ttgcaaactc caattgacat gtcttttgaag ccaaacgatg ctgaatccga aaaggaagtc     600
attgacacca tcttggcttt ggtcaaggat gctaagaacc cagttatctt ggctgatgct     660
tgttgttcca cacacgacgt caaggctgaa actaagaagt tgattgactt gactcaattc     720
ccagctttcg tcaccccaat gggtaagggt tccattgacg aacaacaccc aagatacggt     780
ggtgtttacg tcggtacctt gtccaagcca gaagttaagg aagccgttga atctgctgac     840
ttgattttgt ctgtcggtgc tttgttgtct gatttcaaca ccggttcttt ctcttactct     900
tacaagacca agaacattgt cgaattccac tccgaccaca tgaagatcag aaacgccact     960
ttcccaggtg tccaaatgaa attcgttttg caaaagttgt tgaccactat tgctgacgcc    1020
gctaagggtt acaagccagt tgctgtccca gctagaactc cagctaacgc tgctgtccca    1080
```

-continued

| | |
|---|---|
| gcttctaccc cattgaagca agaatggatg tggaaccaat tgggtaactt cttgcaagaa | 1140 |
| ggtgatgttg tcattgctga aaccggtacc tccgctttcg gtatcaacca aaccactttc | 1200 |
| ccaaacaaca cctacggtat ctctcaagtc ttatggggtt ccattggttt caccactggt | 1260 |
| gctaccttgg gtgctgcttt cgctgctgaa gaaattgatc aaagaagag agttatctta | 1320 |
| ttcattggtg acggttcttt gcaattgact gttcaagaaa tctccaccat gatcagatgg | 1380 |
| ggcttgaagc atacttgtt cgtcttgaac aacgatggtt acaccattga aaagttgatt | 1440 |
| cacggtccaa aggctcaata acgaaatt caaggttggg accacctatc cttgttgcca | 1500 |
| actttcggtg ctaaggacta tgaaacccac agagtcgcta ccaccggtga atgggacaag | 1560 |
| ttgacccaag acaagtcttt caacgacaac tctaagatca gaatgattga aatcatgttg | 1620 |
| ccagtcttcg atgctccaca aaacttggtt gaacaagcta agttgactgc tgctaccaac | 1680 |
| gctaagcaat aa | 1692 |

<210> SEQ ID NO 9
<211> LENGTH: 1776
<212> TYPE: DNA
<213> ORGANISM: Saccharomyces cerevisiae

<400> SEQUENCE: 9

| | |
|---|---|
| atgctaaaat acaaaccttt actaaaaatc tcgaagaact gtgaggctgc tatcctcaga | 60 |
| gcgtctaaga ctagattgaa cacaatccgc gcgtacggtt ctaccgttcc aaaatccaag | 120 |
| tcgttcgaac aagactcaag aaaacgcaca cagtcatgga ctgccttgag agtcggtgca | 180 |
| attctagccg ctactagttc cgtggcgtat ctaaactggc ataatggcca aatagacaac | 240 |
| gagccgaaac tggatatgaa taaacaaaag atttcgcccg ctgaagttgc caagcataac | 300 |
| aagcccgatg attgttgggt tgtgatcaat ggttacgtat acgacttaac gcgattccta | 360 |
| ccaaatcatc caggtgggca ggatgttatc aagtttaacg ccgggaaaga tgtcactgct | 420 |
| attttgaac cactacatgc tcctaatgtc atcgataagt atatagctcc cgagaaaaaa | 480 |
| ttgggtcccc ttcaaggatc catgcctcct gaacttgtct gtcctcctta tgctcctggt | 540 |
| gaaactaagg aagatatcgc tagaaaagaa caactaaaat cgctgctacc tcctctagat | 600 |
| aatattatta acctttacga ctttgaatac ttggcctctc aaactttgac taaacaagcg | 660 |
| tgggcctact attcctccgg tgctaacgac gaagttactc acagagaaaa ccataatgct | 720 |
| tatcatagga tttttttcaa accaaagatc cttgtagatg tacgcaaagt agacatttca | 780 |
| actgacatgt tgggttctca tgtggatgtt cccttctacg tgtctgctac agctttgtgt | 840 |
| aaactgggaa acccccttaga aggtgaaaaa gatgtcgcca gaggttgtgg ccaaggtgtg | 900 |
| acaaaagtcc cacaaatgat atctactttg gcttcatgtt cccctgagga aattattgaa | 960 |
| gcagcaccct ctgataaaca aattcaatgg taccaactat atgttaactc tgatagaaag | 1020 |
| atcactgatg atttggttaa aaatgtgaaa aagctgggtg taaaggcatt atttgtcact | 1080 |
| gtggatgctc caagtttagg tcaaagagaa aaagatatga agctgaaatt ttccaataca | 1140 |
| aaggctggtc caaaagcgat gaagaaaact aatgtagaag aatctcaagg tgcttcgaga | 1200 |
| gcgttatcaa agtttattga ccctctttg acttggaaag atatagaaga gttgaagaaa | 1260 |
| aagacaaaac tacctattgt tatcaaaggt gttcaacgta ccgaagatgt tatcaaagca | 1320 |
| gcagaaatcg gtgtaagtgg ggtggttcta tccaatcatg gtggtagaca attagatttt | 1380 |
| tcaagggctc ccattgaagt cctggctgaa accatgccaa tcctggaaca acgtaacttg | 1440 |
| aaggataagt tggaagtttt cgtggacggt ggtgttcgtc gtggtacaga tgtcttgaaa | 1500 |

-continued

```
gcgttatgtc taggtgctaa aggtgttggt ttgggtagac cattcttgta tgcgaactca    1560
tgctatggtc gtaatggtgt tgaaaaagcc attgaaattt aagagatga aattgaaatg     1620 tctatgagac tattaggtgt tactagcatt gcggaattga agcctgatct tttagatcta    1680
tcaacactaa aggcaagaac agttggagta ccaaacgacg tgctgtataa tgaagtttat    1740
gagggaccta ctttaacaga atttgaggat gcatga                              1776
```

<210> SEQ ID NO 10
<211> LENGTH: 1176
<212> TYPE: DNA
<213> ORGANISM: Saccharomyces cerevisiae

<400> SEQUENCE: 10

```
atgtctgctg ctgctgatag attaaactta acttccggcc acttgaatgc tggtagaaag     60
agaagttcct cttctgtttc tttgaaggct gccgaaaagc ctttcaaggt tactgtgatt    120
ggatctggta actggggtac tactattgcc aaggtggttg ccgaaaattg taagggatac    180
ccagaagttt tcgctccaat agtacaaatg tgggtgttcg aagaagagat caatggtgaa    240
aaattgactg aaatcataaa tactagacat caaaacgtga atacttgcc tggcatcact    300 ctacccgaca atttggttgc taatccagac ttgattgatt cagtcaagga tgtcgacatc    360
atcgttttca acattccaca tcaattttg ccccgtatct gtagccaatt gaaaggtcat    420
gttgattcac acgtcagagc tatctcctgt ctaaagggtt ttgaagttgg tgctaaaggt    480
gtccaattgc tatcctctta catcactgag gaactaggta ttcaatgtgg tgctctatct    540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gaccttactt ccacgttagt gtcatcgaag atgttgctgg tatctccatc    720
tgtggtgctt tgaagaacgt tgttgcctta ggttgtggt tcgtcgaagg tctaggctgg    780
ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccaacctgcgc tggtggtaga aacgtcaagg ttgctaggct aatggctact    960
tctggtaagg acgcctggga atgtgaaaag gagttgttga atggccaatc cgctcaaggt    1020
ttaattacct gcaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                             1176
```

<210> SEQ ID NO 11
<211> LENGTH: 332
<212> TYPE: PRT
<213> ORGANISM: Pelodiscus sinensis japonicus

<400> SEQUENCE: 11

```
Met Ser Val Lys Glu Leu Leu Ile Gln Asn Val His Lys Glu Glu His
1               5                   10                  15

Ser His Ala His Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Arg Gly Glu Met Leu Asp
    50                  55                  60
```

```
Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Ser Asn Pro Val Asp Ile Leu Thr
130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 12
<211> LENGTH: 332
<212> TYPE: PRT
<213> ORGANISM: Ornithorhynchus anatinus

<400> SEQUENCE: 12

Met Ala Gly Val Lys Glu Gln Leu Ile Gln Asn Leu Leu Lys Glu Glu
 1               5                  10                  15

Tyr Ala Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110
```

```
Asn Val Asn Ile Phe Lys Phe Ile Pro Asn Val Val Lys Tyr Ser
            115                 120                 125
Pro Asn Cys Lys Leu Leu Val Val Ser Asn Pro Val Asp Ile Leu Thr
130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
                165                 170                 175
Arg Leu Gly Ile His Ser Thr Ser Cys His Gly Trp Val Ile Gly Glu
            180                 185                 190
His Gly Asp Ser Ser Val Pro Val Trp Ser Gly Val Asn Val Ala Gly
            195                 200                 205
Val Ser Leu Lys Asn Leu His Pro Asp Leu Gly Thr Asp Ala Asp Lys
210                 215                 220
Glu Gln Trp Lys Asp Val His Lys Gln Val Val Asp Ser Ala Tyr Glu
225                 230                 235                 240
Val Ile Lys Leu Lys Gly Tyr Thr Ser Trp Ala Ile Gly Leu Ser Val
                245                 250                 255
Ala Asp Leu Ala Glu Ser Ile Val Lys Asn Leu Arg Arg Val His Pro
            260                 265                 270
Ile Ser Thr Met Ile Lys Gly Leu Tyr Gly Ile Lys Asp Glu Val Phe
            275                 280                 285
Leu Ser Val Pro Cys Val Leu Gly Gln Asn Gly Ile Ser Asp Val Val
            290                 295                 300
Lys Ile Thr Leu Lys Ser Glu Glu Glu Ala His Leu Lys Lys Ser Ala
305                 310                 315                 320
Asp Thr Leu Trp Gly Ile Gln Lys Glu Leu Gln Phe
                325                 330

<210> SEQ ID NO 13
<211> LENGTH: 332
<212> TYPE: PRT
<213> ORGANISM: Tursiops truncatus

<400> SEQUENCE: 13

Met Ala Thr Val Lys Asp Gln Leu Ile Gln Asn Leu Leu Lys Glu Glu
1               5                   10                  15
His Val Pro Gln Asn Lys Ile Thr Val Val Gly Val Gly Ala Val Gly
                20                  25                  30
Met Ala Cys Ala Ile Ser Ile Leu Met Lys Asp Leu Ala Asp Glu Leu
            35                  40                  45
Ala Leu Val Asp Val Ile Glu Asp Lys Leu Lys Gly Glu Met Met Asp
50                  55                  60
Leu Gln His Gly Ser Leu Phe Leu Arg Thr Pro Lys Ile Val Ser Gly
65                  70                  75                  80
Lys Asp Tyr Ser Val Thr Ala Asn Ser Lys Leu Val Ile Ile Thr Ala
                85                  90                  95
Gly Ala Arg Gln Gln Glu Gly Glu Ser Arg Leu Asn Leu Val Gln Arg
            100                 105                 110
Asn Val Asn Ile Phe Lys Phe Ile Val Pro Asn Ile Val Lys Tyr Ser
            115                 120                 125
Pro His Cys Lys Leu Leu Val Val Ser Asn Pro Val Asp Ile Leu Thr
130                 135                 140
Tyr Val Ala Trp Lys Ile Ser Gly Phe Pro Lys Asn Arg Val Ile Gly
145                 150                 155                 160
```

```
                145                 150                 155                 160
        Ser Gly Cys Asn Leu Asp Ser Ala Arg Phe Arg Tyr Leu Met Gly Glu
                        165                 170                 175

Arg Leu Gly Val His Pro Leu Ser Cys His Gly Trp Ile Leu Gly Glu
                        180                 185                 190

His Gly Asp Ser Ser Val Pro Val Trp Ser Gly Val Asn Val Ala Gly
                        195                 200                 205

Val Ser Leu Lys Asn Leu His Pro Glu Leu Gly Thr Asp Ala Asp Lys
                        210                 215                 220

Glu His Trp Lys Ala Ile His Lys Gln Val Val Asp Ser Ala Tyr Glu
        225                 230                 235                 240

Val Ile Lys Leu Lys Gly Tyr Thr Ser Trp Ala Val Gly Leu Ser Val
                        245                 250                 255

Ala Asp Leu Ala Glu Ser Ile Met Lys Asn Leu Arg Arg Val His Pro
                        260                 265                 270

Ile Ser Thr Met Ile Lys Gly Leu Tyr Gly Ile Lys Glu Asp Val Phe
                        275                 280                 285

Leu Ser Val Pro Cys Ile Leu Gly Gln Asn Gly Ile Ser Asp Val Val
                        290                 295                 300

Lys Val Thr Leu Thr Pro Glu Glu Gln Ala Cys Leu Lys Lys Ser Ala
        305                 310                 315                 320

Asp Thr Leu Trp Gly Ile Gln Lys Glu Leu Gln Phe
                        325                 330

<210> SEQ ID NO 14
<211> LENGTH: 332
<212> TYPE: PRT
<213> ORGANISM: Rattus norvegicus

<400> SEQUENCE: 14

Met Ala Ala Leu Lys Asp Gln Leu Ile Val Asn Leu Leu Lys Glu Glu
        1               5                   10                  15

Gln Val Pro Gln Asn Lys Ile Thr Val Val Gly Val Gly Ala Val Gly
                        20                  25                  30

Met Ala Cys Ala Ile Ser Ile Leu Met Lys Asp Leu Ala Asp Glu Leu
                        35                  40                  45

Ala Leu Val Asp Val Ile Glu Asp Lys Leu Lys Gly Glu Met Met Asp
                        50                  55                  60

Leu Gln His Gly Ser Leu Phe Leu Lys Thr Pro Lys Ile Val Ser Ser
        65                  70                  75                  80

Lys Asp Tyr Ser Val Thr Ala Asn Ser Lys Leu Val Ile Ile Thr Ala
                        85                  90                  95

Gly Ala Arg Gln Gln Glu Gly Glu Ser Arg Leu Asn Leu Val Gln Arg
                        100                 105                 110

Asn Val Asn Ile Phe Lys Phe Ile Ile Pro Asn Val Val Lys Tyr Ser
                        115                 120                 125

Pro Gln Cys Lys Leu Leu Ile Val Ser Asn Pro Val Asp Ile Leu Thr
                        130                 135                 140

Tyr Val Ala Trp Lys Ile Ser Gly Phe Pro Lys Asn Arg Val Ile Gly
        145                 150                 155                 160

Ser Gly Cys Asn Leu Asp Ser Ala Arg Phe Arg Tyr Leu Met Gly Glu
                        165                 170                 175

Arg Leu Gly Val His Pro Leu Ser Cys His Gly Trp Val Leu Gly Glu
                        180                 185                 190
```

```
            His Gly Asp Ser Ser Val Pro Val Trp Ser Gly Val Asn Val Ala Gly
                        195                 200                 205

Val Ser Leu Lys Ser Leu Asn Pro Gln Leu Gly Thr Asp Ala Asp Lys
                210                 215                 220

Glu Gln Trp Lys Asp Val His Lys Gln Val Val Asp Ser Ala Tyr Glu
            225                 230                 235                 240

Val Ile Lys Leu Lys Gly Tyr Thr Ser Trp Ala Ile Gly Leu Ser Val
                            245                 250                 255

Ala Asp Leu Ala Glu Ser Ile Met Lys Asn Leu Arg Arg Val His Pro
                        260                 265                 270

Ile Ser Thr Met Ile Lys Gly Leu Tyr Gly Ile Lys Glu Asp Val Phe
                    275                 280                 285

Leu Ser Val Pro Cys Ile Leu Gly Gln Asn Gly Ile Ser Asp Val Val
                290                 295                 300

Lys Val Thr Leu Thr Pro Asp Glu Glu Ala Arg Leu Lys Lys Ser Ala
            305                 310                 315                 320

Asp Thr Leu Trp Gly Ile Gln Lys Glu Leu Gln Phe
                            325                 330

<210> SEQ ID NO 15
<211> LENGTH: 999
<212> TYPE: DNA
<213> ORGANISM: Pelodiscus sinensis japonicus

<400> SEQUENCE: 15
atgtccgtaa aggaactact tatacaaaac gtccataagg aggagcattc tcacgctcac         60
aataagataa cagttgtagg agtaggtgca gtaggtatgg catgtgctat ttcgatatta        120
atgaaagact tggctgatga actagccttg gttgatgtga ttgaggataa gttacgtgga        180
gaaatgttag atttgcaaca tggttcattg ttcttgagaa cccccaaaat tgtctcgggt        240
aaggattatt cagtcactgc tcattctaaa ctggttatca ttacagcagg tgcaagacag        300
caagaagggg agagcagact aaatctggtt caacgtaatg tcaacatctt caagtttatc        360
atcccgaacg tagtaaaata cagtccagac tgcatgttgc ttgttgtgag taatccagtt        420
gacatcttaa cctatgttgc gtggaaaatc agtgggtttc aaaacatag gtgattggc         480 tcaggatgca accttgatag cgccaggttt aggtatctaa tgggagaaaa attaggtatt        540 cactcctat  cttgtcatgg ctggataata ggcgaacatg gtgattcttc ggtacctgtt        600
tggtccgggg ttaatgtggc tggtgttagt ttaaaagcat tatatcctga cctgggtact        660
gatgccgata agaacattg  gaagaagtg  cacaaacaag tggttgattc tgcttacgaa        720
gttattaaac ttaagggcta cacttcttgg gctataggtc tatcagtagc tgatttggca        780
gaaaccgtta tgaaaaattt aagaagagtc cacccaattt ccacgatggt caagggtatg        840
tacggtgtta gctctgacgt cttcttatct gttccttgtg ttttgggata tgcgggaatt        900
acagacgtcg tgaagatgac attgaaatca gaggaagagg aaaaactaag aaagtcagcc        960
gatactctgt ggggcattca aaaggaattg cagttttaa                               999

<210> SEQ ID NO 16
<211> LENGTH: 1267
<212> TYPE: DNA
<213> ORGANISM: Artificial Sequence
<220> FEATURE:
<223> OTHER INFORMATION: Synthetic (ARS/CEN)

<400> SEQUENCE: 16
```

```
gagctccttt catttctgat aaaagtaaga ttactccatt tatcttttca ccaacatatt    60
catagttgaa agttatcctt ctaagtacgt atacaatatt aattaaacgt aaaaacaaaa   120
ctgactgtaa aaatgtgtaa aaaaaaaata tcaaattcat agcagtttca aggaatgaaa   180
actattatga tctggtcacg tgtatataaa ttattaatttt taaacccata taatttatta   240 ttttttttatt ctaaagttta aagtaattttt agtagtattt tatattttga ataaatatac   300
tttaaatttt tatttttata ttttattact tttaaaaata atgttttat ttaaaacaaa   360 attataagtt aaaaagttgt tccgaaagta aaatatattt tatagttttt acaaaaataa   420 attatttta acgtatttt tttaattata ttttgtatg tgattatatc cacaggtatt   480
atgctgaatt tagctgtttc agtttaccag tgtgatagta tgatttttt tgcctctcaa   540 aagctatttt tttagaagct tcgtcttaga aataggtggt gtataaattg cggttgactt   600
ttaactatat atcatttcg atttatttat tacatagaga ggtgcttta attttttaat   660 ttttattttc aataatttta aaagtgggta cttttaaatt ggaacaaagt gaaaaatatc   720
tgttatacgt gcaactgaat tttactgacc ttaaaggact atctcaatcc tggttcagaa   780
atccttgaaa tgattgatat gttggtggat tttctctgat tttcaaacaa gaggtatttt   840
atttcatatt tattatattt tttacattta ttttatattt ttttattgtt tggaagggaa   900
agcgacaatc aaattcaaaa tatattaatt aaactgtaat acttaataag agacaaataa   960
cagccaagaa tcaaatactg ggttttaat caaaagatct ctctacatgc acccaaattc  1020
attatttaaa tttactatac tacagacaga atatcgaac ccagattaag tagtcagacg  1080
cttttccgct ttattgagta tatagcctta catattttct gcccataatt tctggattta  1140
aaataaacaa aaatggttac tttgtagtta tgaaaaaagg cttttccaaa atgcgaaata  1200
cgtgttattt aaggttaatc aacaaaacgc atatccatat gggtagttgg acaaaacttc  1260
aatcgat                                                         1267

<210> SEQ ID NO 17
<211> LENGTH: 289
<212> TYPE: DNA
<213> ORGANISM: Artificial Sequence
<220> FEATURE:
<223> OTHER INFORMATION: Synthetic (CYC promoter)

<400> SEQUENCE: 17
atttggcgag cgttggttgg tggatcaagc ccacgcgtag gcaatcctcg agcagatccg    60
ccaggcgtgt atatatagcg tggatggcca ggcaacttta gtgctgacac atacaggcat   120
atatatatgt gtgcgacgac acatgatcat atggcatgca tgtgctctgt atgtatataa   180
aactcttgtt ttcttctttt ctctaaatat tctttcctta tacattagga cctttgcagc   240
ataaattact atacttctat agacacgcaa acacaaatac acacactaa                289

<210> SEQ ID NO 18
<211> LENGTH: 401
<212> TYPE: DNA
<213> ORGANISM: Artificial Sequence
<220> FEATURE:
<223> OTHER INFORMATION: Synthetic (TEF promoter)

<400> SEQUENCE: 18
atagcttcaa aatgtttcta ctcctttttt actcttccag attttctcgg actccgcgca    60
tcgccgtacc acttcaaaac acccaagcac agcatactaa atttcccctc tttcttcctc   120
tagggtgtcg ttaattaccc gtactaaagg tttggaaaag aaaaaagaga ccgcctcgtt   180
```

```
tcttttctt cgtcgaaaaa ggcaataaaa attttatca cgtttctttt tcttgaaaat    240
tttttttttg attttttct ctttcgatga cctcccattg atatttaagt taataaacgg    300
tcttcaattt ctcaagtttc agtttcattt ttcttgttct attacaactt tttttacttc    360
ttgctcatta gaaagaaagc atagcaatct aatctaagtt t                       401

<210> SEQ ID NO 19
<211> LENGTH: 655
<212> TYPE: DNA
<213> ORGANISM: Artificial Sequence
<220> FEATURE:
<223> OTHER INFORMATION: Synthetic (GPD promoter)

<400> SEQUENCE: 19
agtttatcat tatcaatact cgccatttca agaatacgt aaataattaa tagtagtgat      60
tttcctaact ttatttagtc aaaaaattag ccttttaatt ctgctgtaac ccgtacatgc    120
ccaaaatagg gggcgggtta cacagaatat ataacatcgt aggtgtctgg gtgaacagtt    180
tattcctggc atccactaaa tataatggag cccgcttttt aagctggcat ccagaaaaaa    240
aaagaatccc agcaccaaaa tattgttttc ttcaccaacc atcagttcat aggtccattc    300
tcttagcgca actacagaga acaggggcac aaacaggcaa aaacgggca caacctcaat     360 ggagtgatgc aacctgcctg gagtaaatga tgacacaagg caattgaccc acgcatgtat    420
ctatctcatt ttcttacacc ttctattacc ttctgctctc tctgatttgg aaaaagctga    480 aaaaaaggt tgaaaccagt tccctgaaat tattccccta cttgactaat aagtatataa     540
agacggtagg tattgattgt aattctgtaa atctatttct taaacttctt aaattctact    600
tttatagtta gtctttttt tagttttaaa acaccagaac ttagtttcga cggat          655

<210> SEQ ID NO 20
<211> LENGTH: 1468
<212> TYPE: DNA
<213> ORGANISM: Artificial Sequence
<220> FEATURE:
<223> OTHER INFORMATION: Synthetic (ADH promoter)

<400> SEQUENCE: 20
gccgggatcg aagaaatgat ggtaaatgaa ataggaaatc aaggagcatg aaggcaaaag     60
acaaatataa gggtcgaacg aaaaataaag tgaaagtgt tgatatgatg tatttggctt    120
tgcggcgccg aaaaaacgag tttacgcaat tgcacaatca tgctgactct gtggcggacc    180
cgcgctcttg ccgcccggc gataacgctg gcgtgaggc tgtgcccggc ggagtttttt     240
gcgcctgcat tttccaaggt ttaccctgcg ctaaggggcg agattggaga agcaataaga    300
atgccggttg gggttgcgat gatgacgacc acgacaactg tgtcattat ttaagttgcc     360 gaaagaacct gagtgcattt gcaacatgag tatactagaa gaatgagcca agacttgcga    420
gacgcgagtt tgccggtggt gcgaacaata gagcgaccat gaccttgaag gtgagacgcg    480
cataaccgct agagtacttt gaagaggaaa cagcaatagg gttgctacca gtataaatag    540
acaggtacat acaacactgg aaatggttgt ctgtttgagt acgctttcaa ttcatttggg    600 tgtgcactt attatgttac aatatggaag ggaactttac acttctccta tgcacatata    660
ttaattaaag tccaatgcta gtagagaagg ggggtaacac ccctccgcgc tcttttccga    720
tttttttcta aaccgtggaa tatttcggat atccttttgt tgtttccggg tgtacaatat    780
ggacttcctc ttttctggca accaaaccca tacatcggga ttcctataat accttcgttg    840
```

-continued

```
gtctccctaa catgtaggtg gcggagggga gatatacaat agaacagata ccagacaaga    900
cataatgggc taaacaagac tacaccaatt acactgcctc attgatggtg gtacataacg    960
aactaatact gtagccctag acttgatagc catcatcata tcgaagtttc actacccttt   1020
ttccatttgc catctattga agtaataata ggcgcatgca acttcttttc tttttttttc   1080
ttttctctct cccccgttgt tgtctcacca tatccgcaat gacaaaaaaa tgatggaaga   1140
cactaaagga aaaattaac gacaaagaca gcaccaacag atgtcgttgt tccagagctg    1200
atgaggggta tctcgaagca cacgaaactt tttccttcct tcattcacgc acactactct   1260
ctaatgagca acggtatacg gccttccttc cagttacttg aatttgaaat aaaaaaagt    1320 ttgctgtctt gctatcaagt ataaatagac ctgcaattat taatcttttg tttcctcgtc   1380
attgttctcg ttccctttct tccttgtttc tttttctgca caatatttca agctatacca   1440
agcatacaat caactccaag ctggccgc                                       1468
```

<210> SEQ ID NO 21
<211> LENGTH: 252
<212> TYPE: DNA
<213> ORGANISM: Artificial Sequence
<220> FEATURE:
<223> OTHER INFORMATION: Synthetic (CYC1 terminator)

<400> SEQUENCE: 21

```
tcatgtaatt agttatgtca cgcttacatt cacgccctcc ccccacatcc gctctaaccg     60
aaaaggaagg agttagacaa cctgaagtct aggtccctat ttattttttt atagttatgt    120
tagtattaag aacgttattt atatttcaaa ttttctttt ttttctgtac agacgcgtgt    180
acgcatgtaa cattatactg aaaaccttgc ttgagaaggt tttgggacgc tcgaaggctt    240
taatttgcgg cc                                                        252
```

<210> SEQ ID NO 22
<211> LENGTH: 31
<212> TYPE: DNA
<213> ORGANISM: Artificial Sequence
<220> FEATURE:
<223> OTHER INFORMATION: Synthetic (forward primer)

<400> SEQUENCE: 22

```
cgagctcttc gcggccacct acgccgctat c                                    31
```

<210> SEQ ID NO 23
<211> LENGTH: 32
<212> TYPE: DNA
<213> ORGANISM: Artificial Sequence
<220> FEATURE:
<223> OTHER INFORMATION: Synthetic (reverse primer)

<400> SEQUENCE: 23

```
gctctagata ttgatatagt gtttaagcga at                                   32
```

<210> SEQ ID NO 24
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 24

```
ggatccatgt ccgtaaagga actact                                          26
```

```
<210> SEQ ID NO 25
<211> LENGTH: 34
<212> TYPE: DNA
<213> ORGANISM: Artificial Sequence
<220> FEATURE:
<223> OTHER INFORMATION: Synthetic (reverse primer)

<400> SEQUENCE: 25
acgcgtcgac ttaaaactgc aattcctttt gaat                              34

<210> SEQ ID NO 26
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 26
gagctcaatt aaccctcact aaaggg                                       26

<210> SEQ ID NO 27
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 27
gagctccaaa ttaaagcctt cgagcg                                       26

<210> SEQ ID NO 28
<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 28
aagatctacg aagttgaagg tatgagatgg gctggtaacg ccagtcacga cgttgtaaaa   60

<210> SEQ ID NO 29
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 29
gcttccttaa cttctggctt ggacaaggta ccgacgtaaa aggtttcccg actggaaagc   60

<210> SEQ ID NO 30
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 30
cgatgcgtat tttaagtggt tctctgaaca gcacaatgtc ctcgacacca ccagtcacga   60
cgttgtaaaa                                                         70

<210> SEQ ID NO 31
<211> LENGTH: 72
<212> TYPE: DNA
<213> ORGANISM: Artificial Sequence
<220> FEATURE:
```

<223> OTHER INFORMATION: Synthetic (reverse primer)

<400> SEQUENCE: 31
ggatcacccc ccactcaagt cgttgcattg ctaacatgtg gcattctgcc caaggtttcc    60
cgactggaaa gc    72

<210> SEQ ID NO 32
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 32
ccctatgtct ctggccgatc acgcgccatt gtccctcaga aacaaatcaa ccagtcacga    60
cgttgtaaaa    70

<210> SEQ ID NO 33
<211> LENGTH: 70
<212> TYPE: DNA
<213> ORGANISM: Artificial Sequence
<220> FEATURE:
<223> OTHER INFORMATION: Synthetic (reverse primer)

<400> SEQUENCE: 33
tagaagcaac tgtgccgaca gcctctgaat gagtggtgtt gtaaccaccc aggtttcccg    60
actggaaagc    70

<210> SEQ ID NO 34
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 34
gctcttctct accctgtcat tc    22

<210> SEQ ID NO 35
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 35
tagtgtacag ggtgtcgtat ct    22

<210> SEQ ID NO 36
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 36
ggagttgaag gcaaaattag aagtga    26

<210> SEQ ID NO 37
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 37 attcccttc ctgcacaaca cgagat                                          26

<210> SEQ ID NO 38
<211> LENGTH: 25
<212> TYPE: DNA
<213> ORGANISM: Artificial Sequence
<220> FEATURE:
<223> OTHER INFORMATION: Synthetic (forward primer)

<400> SEQUENCE: 38
tcaatgagac tgttgtcctc ctact                                          25

<210> SEQ ID NO 39
<211> LENGTH: 24
<212> TYPE: DNA
<213> ORGANISM: Artificial Sequence
<220> FEATURE:
<223> OTHER INFORMATION: Synthetic (reverse primer)

<400> SEQUENCE: 39
tacatccttg tcgagccttg ggca                                           24

<210> SEQ ID NO 40
<211> LENGTH: 69
<212> TYPE: DNA
<213> ORGANISM: Artificial Sequence
<220> FEATURE:
<223> OTHER INFORMATION: Synthetic (forward primer)

<400> SEQUENCE: 40
tgagcacgtg agtatacgtg attaagcaca caaaggcagc ttggagtatg gtgctgcaag    60
gcgattaag                                                            69

<210> SEQ ID NO 41
<211> LENGTH: 67
<212> TYPE: DNA
<213> ORGANISM: Artificial Sequence
<220> FEATURE:
<223> OTHER INFORMATION: Synthetic (reverse primer)

<400> SEQUENCE: 41
aggcaagtgc acaaacaata cttaaataaa tactactcag taataacccg gctcgtatgt    60
tgtgtgg                                                              67

<210> SEQ ID NO 42
<211> LENGTH: 21
<212> TYPE: DNA
<213> ORGANISM: Artificial Sequence
<220> FEATURE:
<223> OTHER INFORMATION: Synthetic (forward primer)

<400> SEQUENCE: 42
gccaaatgat ttagcattat c                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic (reverse primer)

<400> SEQUENCE: 43

```
aaaaggagag ggccaagagg g                                              21
```

<210> SEQ ID NO 44
<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 44

```
atgattagac aatcattaat gaaaacagtg tgggctaact ccagtcacga cgttgtaaaa    60
```

<210> SEQ ID NO 45
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 45

```
ctagatagat gaatctctac ccaagaaata aactttagcc aggtttcccg actggaaagc    60
```

<210> SEQ ID NO 46
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 46

```
actgatcatc atttaaaaat gt                                             22
```

<210> SEQ ID NO 47
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 47

```
aaggaaaaaa attttcacac ta                                             22
```

<210> SEQ ID NO 48
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 48

```
atgctgccca gacttggttt tgcgaggact gctaggtcca tacaccgttt ccagtcacga    60
cgttgtaaaa                                                           70
```

<210> SEQ ID NO 49
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 49

```
ctacacggag gaatcccttc caagaaagta aactttggtc aggtttcccg actggaaagc    60
```

<210> SEQ ID NO 50
<211> LENGTH: 20

```
<212> TYPE: DNA
<213> ORGANISM: Artificial Sequence
<220> FEATURE:
<223> OTHER INFORMATION: Synthetic (forward primer)

<400> SEQUENCE: 50
caggaacata gtagaaagac                                                  20

<210> SEQ ID NO 51
<211> LENGTH: 18
<212> TYPE: DNA
<213> ORGANISM: Artificial Sequence
<220> FEATURE:
<223> OTHER INFORMATION: Synthetic (reverse primer)

<400> SEQUENCE: 51
taacgcgaat cttccatg                                                    18

<210> SEQ ID NO 52
<211> LENGTH: 4173
<212> TYPE: DNA
<213> ORGANISM: Artificial Sequence
<220> FEATURE:
<223> OTHER INFORMATION: Synthetic (pUC57-ura3HA vector)

<400> SEQUENCE: 52
gatgacggtg aaaacctctg acacatgcag ctcccggaga cggtcacagc ttgtctgtaa      60
gcggatgccg ggagcagaca agcccgtcag ggcgcgtcag cgggtgttgg cgggtgtcgg     120
ggctggctta actatgcggc atcagagcag attgtactga gagtgcacca tatgcggtgt     180
gaaataccgc acagatgcgt aaggagaaaa taccgcatca ggcgccattc gccattcagg     240
ctgcgcaact gttgggaagg cgatcggtg cgggcctctt cgctattacg ccagctggcg     300 aaaggggat gtgctgcaag gcgattaagt tgggtaacgc cagggttttc ccagtcacga     360
cgttgtaaaa cgacggccag tgaattcgag ctcggtacct cgcgaatgca tctagatatc     420
ggatcccgac gagctgcacc gcggtggcgg ccgtatcttt acccatacg atgttcctga      480 ctatgcgggc tatccctatg acgtcccgga ctatgcagga tcctatccat atgacgttcc     540
agattacgct gctcagtgcg gccgcctgag agtgcaccat accacagctt tcaattcaa      600 ttcatcattt tttttttatt cttttttttg atttcggttt ctttgaaatt ttttgattc      660 ggtaatctcc gaacagaagg aagaacgaag gaaggagcac agacttagat tggtatatat     720
acgcatatgt agtgttgaag aaacatgaaa ttgcccagta ttcttaaccc aactgcacag     780
aacaaaaacc tgcaggaaac gaagataaat catgtcgaaa gctacatata aggaacgtgc     840
tgctactcat cctagtcctg ttgctgccaa gctatttaat atcatgcacg aaaagcaaac     900
aaacttgtgt gcttcattgg atgttcgtac caccaaggaa ttactggagt tagttgaagc     960
attaggtccc aaaatttgtt tactaaaaac acatgtggat atcttgactg attttttccat    1020 ggagggcaca gttaagccgc taaaggcatt atccgccaag tacaattttt tactcttcga    1080
agacagaaaa tttgctgaca ttggtaatac agtcaaattg cagtactctg cggtgtata     1140 cagaatagca gaatgggcag acattacgaa tgcacacggt gtggtgggcc caggtattgt    1200
tagcggtttg aagcaggcgg cagaagaagt aacaaaggaa cctagaggcc ttttgatgtt    1260
agcagaattg tcatgcaagg ctccctatc tactggagaa tatactaagg gtactgttga    1320
cattgcgaag agcgacaaag attttgttat cggctttatt gctcaaagag acatgggtgg    1380
aagagatgaa ggttacgatt ggttgattat gacacccggt gtgggtttag atgacaaggg    1440
```

```
agacgcattg ggtcaacagt atagaaccgt ggatgatgtg gtctctacag gatctgacat   1500
tattattgtt ggaagaggac tatttgcaaa gggaagggat gctaaggtag agggtgaacg   1560
ttacagaaaa gcaggctggg aagcatattt gagaagatgc ggccagcaaa actaaaaaac   1620
tgtattataa gtaaatgcat gtatactaaa ctcacaaatt agagcttcaa tttaattata   1680
tcagttatta ccctatgcgg tgtgaaatac cgcacagatg cgtaaggaga aaataccgca   1740
tcaggaaatt gtagcggccg cgaatttgag cttatctttt acccatacga tgttcctgac   1800
tatgcgggct atccctatga cgtcccggac tatgcaggat cctatccata tgacgttcca   1860
gattacgcta ctagcggggg gcccggtgac gggcccgtcg actgcagagg cctgcatgca   1920
agcttggcgt aatcatggtc atagctgttt cctgtgtgaa attgttatcc gctcacaatt   1980
ccacacaaca tacgagccgg aagcataaag tgtaaagcct ggggtgccta atgagtgagc   2040
taactcacat taattgcgtt gcgctcactg cccgctttcc agtcgggaaa cctgtcgtgc   2100
cagctgcatt aatgaatcgg ccaacgcgcg gggagaggcg gtttgcgtat tgggcgctct   2160
tccgcttcct cgctcactga ctcgctgcgc tcggtcgttc ggctgcggcg agcggtatca   2220
gctcactcaa aggcggtaat acggttatcc acagaatcag gggataacgc aggaaagaac   2280
atgtgagcaa aaggccagca aaaggccagg aaccgtaaaa aggccgcgtt gctggcgttt   2340
ttccataggc tccgcccccc tgacgagcat cacaaaaatc gacgctcaag tcagaggtgg   2400
cgaaacccga caggactata aagataccag gcgtttcccc ctggaagctc cctcgtgcgc   2460
tctcctgttc cgaccctgcc gcttaccgga tacctgtccg cctttctccc ttcgggaagc   2520
gtggcgcttt ctcatagctc acgctgtagg tatctcagtt cggtgtaggt cgttcgctcc   2580
aagctgggct gtgtgcacga accccccgtt cagcccgacc gctgcgcctt atccggtaac   2640
tatcgtcttg agtccaaccc ggtaagacac gacttatcgc cactggcagc agccactggt   2700
aacaggatta gcagagcgag gtatgtaggc ggtgctacag agttcttgaa gtggtggcct   2760
aactacggct acactagaag aacagtattt ggtatctgcg ctctgctgaa gccagttacc   2820
ttcggaaaaa gagttggtag ctcttgatcc ggcaaacaaa ccaccgctgg tagcggtggt   2880
ttttttgttt gcaagcagca gattacgcgc agaaaaaaag gatctcaaga agatcctttg   2940
atcttttcta cggggtctga cgctcagtgg aacgaaaact cacgttaagg gattttggtc   3000
atgagattat caaaaaggat cttcacctag atccttttaa attaaaaatg aagttttaaa   3060
tcaatctaaa gtatatatga gtaaacttgg tctgacagtt accaatgctt aatcagtgag   3120
gcacctatct cagcgatctg tctatttcgt tcatccatag ttgcctgact ccccgtcgtg   3180
tagataacta cgatacggga gggcttacca tctggcccca gtgctgcaat gataccgcga   3240
gacccacgct caccggctcc agatttatca gcaataaacc agccagccgg aagggccgag   3300
cgcagaagtg gtcctgcaac tttatccgcc tccatccagt ctattaattg ttgccgggaa   3360
gctagagtaa gtagttcgcc agttaatagt ttgcgcaacg ttgttgccat tgctacaggc   3420
atcgtggtgt cacgctcgtc gtttggtatg gcttcattca gctccggttc ccaacgatca   3480
aggcgagtta catgatcccc catgttgtgc aaaaaagcgg ttagctcctt cggtcctccg   3540
atcgttgtca gaagtaagtt ggccgcagtg ttatcactca tggttatggc agcactgcat   3600
aattctctta ctgtcatgcc atccgtaaga tgcttttctg tgactggtga gtactcaacc   3660
aagtcattct gagaatagtg tatgcggcga ccgagttgct cttgcccggc gtcaatacgg   3720
gataataccg cgccacatag cagaacttta aaagtgctca tcattggaaa acgttcttcg   3780
gggcgaaaac tctcaaggat cttaccgctg ttgagatcca gttcgatgta acccactcgt   3840
```

```
gcacccaact gatcttcagc atcttttact ttcaccagcg tttctgggtg agcaaaaaca   3900
ggaaggcaaa atgccgcaaa aagggaata agggcgacac ggaaatgttg aatactcata   3960
ctcttccttt ttcaatatta ttgaagcatt tatcagggtt attgtctcat gagcggatac   4020
atatttgaat gtatttagaa aaataaacaa atagggttc cgcgcacatt tccccgaaaa   4080
gtgccacctg acgtctaaga aaccattatt atcatgacat taacctataa aaataggcgt   4140
atcacgaggc cctttcgtct cgcgcgtttc ggt                                4173
```

<210> SEQ ID NO 53
<211> LENGTH: 3873
<212> TYPE: DNA
<213> ORGANISM: Artificial Sequence
<220> FEATURE:
<223> OTHER INFORMATION: Synthetic (pUC19-HIS3 vector)

<400> SEQUENCE: 53

```
agctcggtac ccggggatcc tctagagtcg acaattcccg ttttaagagc ttggtgagcg     60
ctaggagtca ctgccaggta cgtttgaac acggcattag tcagggaagt cataacacag    120
tcctttcccg caattttctt tttctattac tcttggcctc ctctagtaca ctctatattt    180
ttttatgcct cggtaatgat tttcatttt tttttttccc tagcggatga ctcttttttt    240
ttcttagcga ttggcattat cacataatga attatacatt atataaagta atgtgatttc    300
ttcgaagaat atactaaaaa atgagcaggc aagataaacg aaggcaaaga tgacagagca    360
gaaagcccta gtaaagcgta ttacaaatga accaagatt cagattgcga tctctttaaa    420
gggtggtccc ctagcgatag agcactcgat cttcccagaa aaagaggcag aagcagtagc    480
agaacaggcc acacaatcgc aagtgattaa cgtccacaca ggtatagggt ttctggacca    540
tatgatacat gctctggcca agcattccgg ctggtcgcta atcgttgagt gcattggtga    600
cttacacata gacgaccatc acaccactga agactgcggg attgctctcg gtcaagcttt    660
taaagaggcc ctactggcgc gtggagtaaa aaggtttgga tcaggatttg cgcctttgga    720
tgaggcactt tccagagcgg tggtagatct ttcgaacagg ccgtacgcag ttgtcgaact    780
tggtttgcaa agggagaaag taggagatct ctcttgcgag atgatcccgc attttcttga    840
aagctttgca gaggctagca gaattaccct ccacgttgat tgtctgcgag gcaagaatga    900
tcatcaccgt agtgagagtg cgttcaaggc tcttgcggtt gccataagag aagccacctc    960
gcccaatggt accaacgatg ttccctccac caaaggtgtt cttatgtagt gacaccgatt   1020
atttaaagct gcagcatacg atatatatac atgtgtatat atgtatacct atgaatgtca   1080
gtaagtatgt atacgaacag tatgatactg aagatgacaa ggtaatgcat cattctatac   1140
gtgtcattct gaacgaggcg cgctttcctt ttttctttt gcttttctt ttttttctc     1200 ttgaactcga cgggtcgacc tgcaggcatg caagcttggc gtaatcatgg tcatagctgt   1260
ttcctgtgtg aaattgttat ccgctcacaa ttccacacaa catacgagcc ggaagcataa   1320
agtgtaaagc ctggggtgcc taatgagtga gctaactcac attaattgcg ttgcgctcac   1380
tgcccgcttt ccagtcggga aacctgtcgt gccagctgca ttaatgaatc ggccaacgcg   1440
cggggagagg cggtttgcgt attgggcgct cttccgcttc ctcgctcact gactcgctgc   1500
gctcggtcgt tcggctgcgg cgagcggtat cagctcactc aaaggcggta atacggttat   1560
ccacagaatc aggggataac gcaggaaaga acatgtgagc aaaaggccag caaaaggcca   1620
ggaaccgtaa aaaggccgcg ttgctggcgt ttttccatag gctccgcccc cctgacgagc   1680
```

```
atcacaaaaa tcgacgctca agtcagaggt ggcgaaaccc gacaggacta taaagatacc   1740
aggcgtttcc ccctggaagc tccctcgtgc gctctcctgt tccgaccctg ccgcttaccg   1800
gatacctgtc cgcctttctc ccttcgggaa gcgtggcgct ttctcatagc tcacgctgta   1860
ggtatctcag ttcggtgtag gtcgttcgct ccaagctggg ctgtgtgcac gaaccccccg   1920
ttcagcccga ccgctgcgcc ttatccggta actatcgtct tgagtccaac ccggtaagac   1980
acgacttatc gccactggca gcagccactg gtaacaggat tagcagagcg aggtatgtag   2040
gcggtgctac agagttcttg aagtggtggc ctaactacgg ctacactaga agaacagtat   2100
ttggtatctg cgctctgctg aagccagtta ccttcggaaa aagagttggt agctcttgat   2160
ccggcaaaca accaccgct ggtagcggtg gttttttttgt ttgcaagcag cagattacgc   2220
gcagaaaaaa aggatctcaa gaagatcctt tgatcttttc tacggggtct gacgctcagt   2280
ggaacgaaaa ctcacgttaa gggattttgg tcatgagatt atcaaaaagg atcttcacct   2340
agatcctttt aaattaaaaa tgaagtttta atcaatcta aagtatatat gagtaaactt    2400
ggtctgacag ttaccaatgc ttaatcagtg aggcacctat ctcagcgatc tgtctatttc   2460
gttcatccat agttgcctga ctccccgtcg tgtagataac tacgatacgg agggcttac    2520
catctggccc cagtgctgca atgataccgc gagacccacg ctcaccggct ccagatttat   2580
cagcaataaa ccagccagcc ggaagggccg agcgcagaag tggtcctgca actttatccg   2640
cctccatcca gtctattaat tgttgccggg aagctagagt aagtagttcg ccagttaata   2700
gtttgcgcaa cgttgttgcc attgctacag gcatcgtggt gtcacgctcg tcgtttggta   2760
tggcttcatt cagctccggt tcccaacgat caaggcgagt tacatgatcc cccatgttgt   2820
gcaaaaaagc ggttagctcc ttcggtcctc cgatcgttgt cagaagtaag ttggccgcag   2880
tgttatcact catggttatg gcagcactgc ataattctct tactgtcatg ccatccgtaa   2940
gatgcttttc tgtgactggt gagtactcaa ccaagtcatt ctgagaatag tgtatgcggc   3000
gaccgagttg ctcttgcccg gcgtcaatac gggataatac cgcgccacat agcagaactt   3060
taaaagtgct catcattgga aaacgttctt cggggcgaaa actctcaagg atcttaccgc   3120
tgttgagatc cagttcgatg taacccactc gtgcacccaa ctgatcttca gcatctttta   3180
ctttcaccag cgtttctggg tgagcaaaaa caggaaggca aaatgccgca aaaaagggaa   3240
taagggcgac acggaaatgt tgaatactca tactcttcct ttttcaatat tattgaagca   3300
tttatcaggg ttattgtctc atgagcggat acatatttga atgtatttag aaaaataaac   3360
aaataggggt tccgcgcaca tttccccgaa aagtgccacc tgacgtctaa gaaaccatta   3420
ttatcatgac attaacctat aaaaataggc gtatcacgag gccctttcgt ctcgcgcgtt   3480
tcggtgatga cggtgaaaac ctctgacaca tgcagctccc ggagacggtc acagcttgtc   3540
tgtaagcgga tgccgggagc agacaagccc gtcagggcgc gtcagcgggt gttggcgggt   3600
gtcgggctg gcttaactat gcggcatcag agcagattgt actgagagtg caccatatgc   3660
ggtgtgaaat accgcacaga tgcgtaagga gaaaataccg catcaggcgc cattcgccat   3720
tcaggctgcg caactgttgg gaagggcgat cggtgcgggc ctcttcgcta ttacgccagc   3780
tggcgaaagg gggatgtgct gcaaggcgat taagttgggt aacgccaggg ttttcccagt   3840
cacgacgttg taaaacgacg gccagtgaat tcg                                3873
```

<210> SEQ ID NO 54
<211> LENGTH: 31
<212> TYPE: DNA
<213> ORGANISM: Artificial Sequence

```
<220> FEATURE:
<223> OTHER INFORMATION: Synthetic (primer)

<400> SEQUENCE: 54
cctcctgagt cgacaattcc cgtttttaaga g                              31

<210> SEQ ID NO 55
<211> LENGTH: 30
<212> TYPE: DNA
<213> ORGANISM: Artificial Sequence
<220> FEATURE:
<223> OTHER INFORMATION: Synthetic (primer)

<400> SEQUENCE: 55
cgaccgtggt cgacccgtcg agttcaagag                                 30
```

# YEAST CELL WITH INACTIVATED NADH DEHYDROGENASE AND METHOD OF PRODUCING LACTATE USING THE YEAST CELL

CROSS-REFERENCE TO RELATED APPLICATIONS

This application claims the benefit of Korean Patent Application No. 10-2013-0085520, filed on Jul. 19, 2013, in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 71,573 bytes ASCII (Text) file named "718199_ST25.TXT," created Jul. 14, 2014.

BACKGROUND

1. Field

The present disclosure relates to a yeast cell with inactivated NADH dehydrogenase and a method of producing lactate using the yeast cell.

2. Description of the Related Art

Lactate is an organic acid that is broadly used in various industrial fields, such as food, pharmaceutics, chemicals, and electronics. Lactate is colorless, odorless, and a low-volatile material that dissolves well in water. Lactate is non-toxic to the human body and thus may be used as a flavor agent, a taste agent, or a preserving agent. Also, lactate is an environment-friendly alternative polymer material and a raw material of a polylactic acid (PLA), a biodegradable plastic.

PLA is a polyester-based resin that is obtained by ring opening polymerization (ROP) of lactide, a dimer which has been converted from lactic acid. PLA may be variously processed into a film, sheet, fiber, plastic, etc. Thus, demands for PLA as bioplastic have recently increased to broadly replace conventional typical petrochemical plastics, such as polyethylene (PE), polypropylene (PP), polyethylene terephthalate (PET), or polystyrene (PS).

In addition, lactate includes both a hydroxyl group and a carboxyl group and thus is highly reactive. Accordingly, lactate is easily converted into an industrially important compound, such as lactate ester, acetaldehyde, or propyleneglycol, and thus has received attention as an alternative chemical material of the next generation in chemical industry.

Currently, lactate is produced by an industrially petrochemical synthesis process and a biotechnological fermentation process. The petrochemical synthesis process is performed by oxidizing ethylene derived from crude oil, preparing lactonitrile through addition of hydrogen cyanide after acetaldehyde, purifying by distillation, and hydrolyzing by using chloric acid or phosphoric acid. The biotechnological fermentation process is used to manufacture lactate from a reproducible carbon hydrate, such as, starch, sucrose, maltose, glucose, fructose, or xylose, as a substrate.

Therefore, a strain for efficiently producing lactate and a lactate production method using such a strain are needed.

SUMMARY

Provided is a genetically engineered yeast cell in which the activity of a protein having a sequence identity of about 95% or more to an external mitochondrial NADH dehydrogenase is decreased compared to a parent cell of the genetically engineered yeast cell. The genetically engineered yeast cell, in one embodiment, exhibits an improved ability of producing lactate.

Also provided is a method of efficiently producing lactate by using the yeast cell, wherein the method comprises culturing the genetically engineered yeast cell of claim 1, whereby the yeast produces lactate; and collecting lactate from the culture.

Further provided is method of enhancing lactate production in a lactate-producing yeast, the method comprising inactivating the expression of an external mitochondrial NADH dehydrogenase in the yeast.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
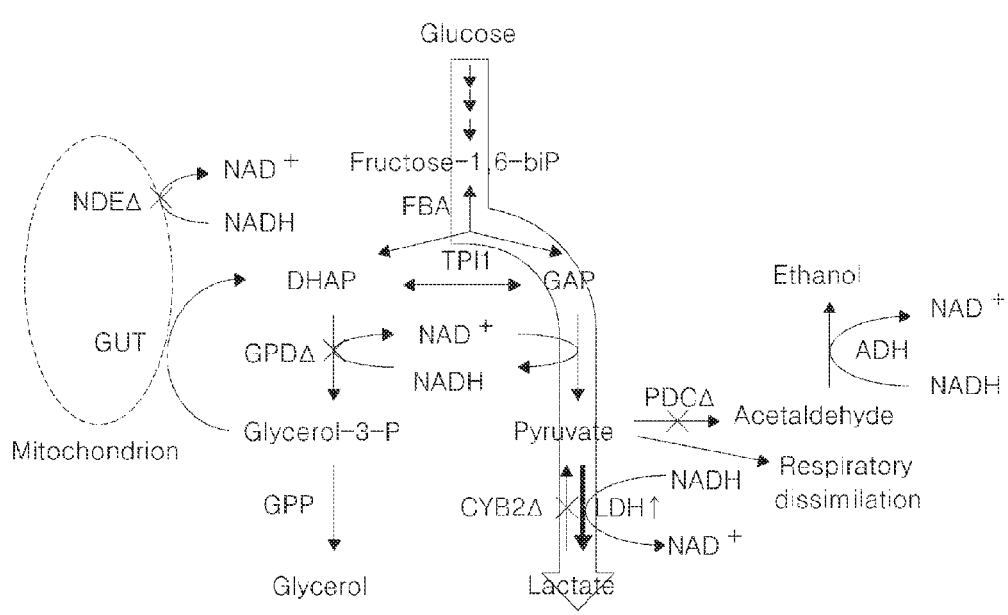
FIG. 1 is a diagram illustrating a lactate production pathway of a yeast cell having an ability of producing lactate.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

According to an aspect of the present disclosure, provided is a yeast cell (e.g., a genetically engineered yeast cell) capable of producing lactate, the yeast cell in which the activity of a protein having a sequence identity of about 95% or more to an external mitochondrial NADH dehydrogenase is inactivated or decreased compared to a parent cell (e.g., a non-genetically engineered yeast cell of the same type).

As used herein, the expression "increase in activity" or "increased activity" of a cell, protein, or enzyme may refer to a detectable increase in the activity thereof. "Increased activity" or "increase in activity" may also refer to an activity level of a modified (e.g., genetically engineered) cell, protein, or enzyme that is higher than that of a comparative cell, protein, or enzyme of the same type, such as a cell, protein, or enzyme that does not have a given modification (e.g., the original or "wild-type" cell, protein, or enzyme). For example, the activity of a modified or engineered cell, protein, or enzyme may be increased by about 5% or more, about 10% or more, about 15% or more, about 20% or more, about 30% or more, about 50% or more, about 60% or more, about 70% or more, or about 100% than the activity of a non-engineered cell, protein, or enzyme of the same type, i.e., a wild-type cell, protein, or enzyme. The activity of a specific protein or enzyme in a cell may be increased by about 5% or more, about 10% or more, about 15% or more, about 20% or more, about 30% or more, about 50% or more, about 60% or more, about 70% or more, or about 100% than the activity of the same protein or enzyme in a parent cell, e.g., non-engineered cell. A cell with increased activity of a protein or an enzyme may be identified by using a method known in the art.

Meanwhile, as used herein, an "inactivated" or "decreased" activity denotes a cell having an activity of an enzyme or polypeptide that is lower than that measured in a parent cell (e.g., a non-genetically engineered cell). Also, an "inactivated" or "decreased" activity denotes an isolated enzyme, or a polypeptide having an activity that is lower than that of original or "wild-type" enzyme or a polypeptide. Inactivated or decreased activity encompasses no activity. For example, an enzyme conversion activity from a substrate to a product with respect to a modified (e.g., genetically engineered) cell or enzyme may be about 20% or more, about 30% or more, about 40% or more, about 50% or more, about 55% or more, about 60% or more, about 70% or more, about 75% or more, about 80% or more, about 85% or more, about 90% or more, about 95% or more, or about 100% decreased as compared to the enzyme conversion activity of a cell or enzyme that does not have the modification, i.e., parent cell or "wild-type" cell or enzyme. Decreased activity of an enzyme or cell may be confirmed by methods known in the art. The inactivation or decrease in activity includes the case when a gene-encoding enzyme is not expressed or has a lower amount of expression compared to a cell including the gene that is not modified, i.e., a parent cell or "wild-type" cell, when an activity of the enzyme is removed or decreased even when the enzyme is expressed in a specific cell.

The term "parent cell" refers to an original cell, for example, a non-engineered cell of the same type as an engineered yeast cell. With respect to a particular genetic modification, the "parent cell" can be a cell that lacks the particular genetic modification, but is identical in all other respects. Thus, a parent cell can be a cell used as starting material to produce a genetically engineered yeast cell having an inactivated or decreased activity of a given protein (e.g., a protein having a sequence identity of about 95% or more to an external mitochondrial NADH dehydrogenase). By way of further illustration, with respect to a yeast cell in which a gene encoding external NADH dehydrogenase has been modified to reduce external NADH dehydrogenase activity in the cell, the parent cell can be a yeast cell comprising an unaltered, "wild-type" external NADH dehydrogenase gene. The same comparison applies to other genetic modifications.

An activity of the enzyme may be inactivated or decreased by deletion or disruption of a gene encoding the enzyme. The "deletion" or "disruption" of a gene as used herein refers to mutation of part or all of the gene, or part or all of a regulatory sequence of the gene, such as a promoter or a terminator region thereof, such that the gene is not expressed or is expressed at a reduced level, or expresses a gene product (e.g., enzyme) with no activity or reduced activity as compared to the naturally occurring gene product. The mutation may include addition, substitution, insertion, deletion, or conversion of at least one nucleotide of the gene. The deletion or disruption of a gene may be achieved by genetic manipulation such as homologous recombination, directed mutagenesis, or molecular evolution. When a cell includes a plurality of the same genes, or two or more different paralogs of a gene, one or more of the genes may be removed or disrupted. For example, inactivation or decrease of the enzyme may be caused by homologous recombination or may be performed by transforming the cell with a vector including a part of sequence of the gene to the cell, culturing the cell so that the sequence may homogonously recombine with an endogenous gene of the cell so as to delete or disrupt the gene, and then selecting cells, in which homologous recombination occurred, using a selection marker.

As used herein, the term "gene" denotes a nucleic acid fragment expressing a specific protein, and the fragment may or may not include a regulatory sequence of a 5'-non coding sequence and/or 3'-non coding sequence.

A sequence identity of a nucleic acid or polypeptide refers to the extent of identity between bases or amino acid residues of sequences obtained after the sequences are aligned so as to best match in certain comparable regions. The sequence identity is a value obtained by comparison of two sequences in certain comparable regions via optimal alignment of the two sequences, wherein portions of the sequences in the certain comparable regions may be added or deleted compared to reference sequences. A percentage of sequence identity may be calculated by, for example, comparing two optimally aligned sequences in the entire comparable regions, determining the number of locations in which the same amino acids or nucleic acids appear to obtain the number of matching locations, dividing the number of the matching locations by the total number of locations in the comparable regions (that is, the size of a range), and multiplying the result of the division by 100 to obtain the percentage of the sequence identity. The percentage of the sequence identity may be determined using a known sequence comparison program, for example, BLASTN or BLASTP (NCBI), CLC Main Workbench (CLC bio), and MegAlign™ (DNASTAR Inc.).

Various levels of sequence identity may be used to identify various types of polypeptides or polynucleotides having the same or similar functions. For example, a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100% may be used.

The yeast cell may be Ascomycota. The Ascomycota may be Saccharomycetaceae. The Saccharomycetaceae may be *Saccharomyces* genus, *Kluyveromyces* genus, *Candida* genus, *Pichia* genus, *Issatchenkia* genus, *Debaryomyces* genus, *Zygosaccharomyces* genus, or *Saccharomycopsis* genus. The *Saccharomyces* genus may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum,* or *S. zonatus*. The *Kluyveromyces* genus may be *Kluyveromyces thermotolerans*. The *Candida* genus may be *Candida glabrata*. The *Zygosaccharomyces* genus may be *Zygosaccharomyces bailli* or *Zygosaccharomyces rouxii*.

The yeast cell (e.g., a genetically engineered yeast cell) may have an ability to produce lactate. The activity of an external mitochondrial NADH dehydrogenase is sufficiently inactivated or decreased to allow the yeast to produce lactate, or to improve lactate production in a yeast cell that otherwise produces lactate.

The external mitochondrial NADH dehydrogenase may be an enzyme that is classified as EC. 1.6.5.9 or EC. 1.6.5.3. The NADH dehydrogenase may be a type II NADH:ubiquinone oxidoreductase. An "external" NADH dehydrogenase may be an NADH dehydrogenase located on the outer surface of the inner mitochondrial membrane facing the cytoplasm. The NADH dehydrogenase may be an enzyme that catalyzes oxidation of cytosolic NADH to NAD+. The NADH dehydrogenase may re-oxidize cytosolic NADH formed by glycolysis process. The NADH dehydrogenase may provide cytosolic NADH to a mitochondrial respiratory chain. The NADH dehydrogenase may be NDE1, NDE2, or a combination thereof. The NADH dehydrogenase may be distinguished from an internal mitochondrial NADH dehydrogenase NDI1 that is present and functions inside mitochondria. The NDE1 and NDE2 may each, respectively, have a sequence identity of at least 75%, at least 80%, at least 85%, at least 90%, at least 95%, at least 96%, at least 97%, at least 98%, at least 99%, or 100% to amino acid sequences of SEQ ID NO: 1 and SEQ ID NO: 2. A gene encoding NDE1 and a gene encoding NDE2 may, each respectively, have a sequence identity of at least 75%, at least 80%, at least 85%, at least 90%, at least 95%, at least 96%, at least 97%, at least 98%, at least 99%, or 100% to nucleotide sequences of SEQ ID NO: 3 and SEQ ID NO: 4.

In the yeast cell (e.g., a genetically engineered yeast cell), the activity of polypeptide that converts pyruvate to acetaldehyde, a polypeptide that converts lactate to pyruvate, a polypeptide that converts dihydroxyacetone phosphate (DHAP) to glycerol-3-phosphate, or a combination thereof, may be inactivated or decreased. In the yeast cell (e.g., a genetically engineered yeast cell), the activity of polypeptide that converts pyruvate to acetaldehyde; the activity of a polypeptide that converts lactate to pyruvate; the activity of a polypeptide that converts dihydroxyacetone phosphate (DHAP) to glycerol-3-phosphate; the activity of polypeptide that converts pyruvate to acetaldehyde, and the activity of a polypeptide that converts lactate to pyruvate; or the activity of polypeptide that converts pyruvate to acetaldehyde; the activity of a polypeptide that converts lactate to pyruvate; the activity of a polypeptide that converts dihydroxyacetone phosphate (DHAP) to glycerol-3-phosphate, may be inactivated or decreased.

In the yeast cell (e.g., a genetically engineered yeast cell), an activity of polypeptide that converts pyruvate to acetaldehyde may be inactivated or decreased. The polypeptide that converts pyruvate to acetaldehyde may be an enzyme that is classified as EC 4.1.1.1. The polypeptide that converts pyruvate to acetaldehyde may have at least 75%, at least 80%, at least 85%, at least 90%, at least 95%, at least 96%, at least 97%, at least 98%, at least 99%, or 100% of sequence identity with an amino acid sequence of SEQ ID NO: 5. The gene that encodes the polypeptide that converts pyruvate to acetaldehyde may have a sequence identity of at least 75%, at least 80%, at least 85%, at least 90%, at least 95%, at least 96%, at least 97%, at least 98%, at least 99%, or 100% to an nucleotide sequence of SEQ ID NO: 8. The gene may be an enzyme that encodes pyruvate decarboxylase (e.g., PDC). Examples of PDC proteins include PDC1, PDC5 and PDC6. In the yeast cell (e.g., a genetically engineered yeast cell), an activity of alcohol dehydrogenase (e.g., ADH) that catalyzes converting acetaldehyde to ethanol may be inactivated or decreased. Examples of ADH proteins include ADH1, ADH2, ADH3, ADH4, ADH5, ADH6, and ADH7. The alcohol dehydrogenase may be NADH dependent.

In the yeast cell (e.g., a genetically engineered yeast cell), an activity of the polypeptide that converts lactate to pyruvate may be inactivated or decreased. The polypeptide that converts lactate to pyruvate may be a cytochrome c-dependent enzyme. The polypeptide that converts lactate to pyruvate may be cytochrome c-oxidoreductase (CYB2). The lactate cytochrome c-oxidoreductase may be an enzyme that is classified as EC 1.1.2.4 that acts on D-lactate or EC 1.1.2.3 that acts on L-lactate. The polypeptide that converts lactate to pyruvate may have a sequence identity of at least 75%, at least 80%, at least 85%, at least 90%, at least 95%, at least 96%, at least 97%, at least 98%, at least 99%, or 100% to an amino acid sequence of SEQ ID NO: 6. A gene encoding the polypeptide that converts lactate to pyruvate may have a sequence identity of at least 75%, at least 80%, at least 85%, at least 90%, at least 95%, at least 96%, at least 97%, at least 98%, at least 99%, or 100% to a nucleotide sequence of SEQ ID NO: 9.

In the yeast cell (e.g., a genetically engineered yeast cell), an activity of the polypeptide that converts DHAP to glycerol-3-phosphate may be inactivated or decreased. The polypeptide that converts DHAP to glycerol-3-phosphate may be a cytosolic glycerol-3-phosphate dehydrogenase (GPD), which is an enzyme that catalyzes reduction of DHAP to glycerol-3-phosphate by using oxidation of NADH to NAD+. The GPD may belong to EC 1.1.1.8. Examples of GPD proteins include GPD1 and GPD2. The GPD may have a sequence identity of at least 75%, at least 80%, at least 85%, at least 90%, at least 95%, at least 96%, at least 97%, at least 98%, at least 99%, or 100% to an amino acid sequence of SEQ ID NO: 7. The gene encoding the GPD may have a sequence identity of at least 75%, at least 80%, at least 85%, at least 90%, at least 95%, at least 96%, at least 97%, at least 98%, at least 99%, or 100% to a nucleotide sequence of SEQ ID NO: 10.

In the yeast cell (e.g., a genetically engineered yeast cell), an activity of converting pyruvate to lactate may be increased. The activity of converting pyruvate to lactate may be sufficiently increased to produce lactate. Thus, the yeast cell (e.g., a genetically engineered yeast cell) may be capable of producing lactate from pyruvate.

The activity of converting pyruvate to lactate may be increased by increasing expression of a gene encoding a polypeptide that converts pyruvate to lactate. Expression may be increased by an introduction of a gene encoding polypeptide that converts pyruvate to lactate into the yeast cell (e.g., an exogenous gene) and/or by increasing expression of an endogenous gene encoding polypeptide that converts pyruvate to lactate. The increase in expression may be caused by an increased number of copies of the gene, or by mutation of a regulatory region of the gene. The increase in the copy number of the gene may be caused by amplification of one or more endogenous genes or by introduction of one or more exogenous genes. The mutation of the regulatory region of the gene may be caused by mutation of a regulatory region of the endogenous gene. The mutation of the regulatory region of the gene may include the replacement of the original promoter region with a stronger promoter, such as a CYC promoter, a TEF promoter, a GPD promoter, and an ADH promoter. The CYC promoter, TEF promoter, GPD promoter, and ADH promoter may be, each respectively, have nucleotide sequences of SEQ ID NO: 17, 18, 19, and 20. The replacement may be achieved by genetic manipulation such as homologous recombination, directed mutagenesis, or molecular evolution. The replacement may be achieved with or without introduction of other gene such as LDH gene. The exogenous gene may be a homogenous or heterogenous gene.

The polypeptide converting pyruvate to lactate may be a lactate dehydrogenase (LDH). The lactate dehydrogenase may be a catalyst that increases the conversion of pyruvate to lactate. The lactate dehydrogenase may be an NAD(P)-dependent enzyme, or may function on L-lactate or D-lactate. The NAD(P)-dependent enzyme may be an enzyme that is classified into EC 1.1.1.27 that functions on L-lactate or EC 1.1.1.28 that functions on D-lactate.

The polynucleotide encoding the lactate dehydrogenase may be an enzyme derived from bacteria, yeast, fungus, an animal such mammal, amphibian, or Sauropsida. The polynucleotide may be a polynucleotide that encodes at least one LDH selected from LDHs derived from *Pelodiscus sinensis japonicus, Ornithorhynchus anatinus, Tursiops truncatus, Rattus norvegicus*, and *Xenopus laevis*. A lactate dehydrogenase derived from *Pelodiscus sinensis japonicas*, a lactate dehydrogenase derived from *Ornithorhynchus anatinus*, a lactate dehydrogenase derived from *Tursiops truncatus*, a lactate dehydrogenase derived from *Rattus norvegicus*, and a lactate dehydrogenase derived from *Xenopus laevis* may each, respectively, have amino acid sequences of SEQ ID NO: 11, 12, 13, and 14. The lactate dehydrogenase may have at least 75%, at least 80%, at least 85%, at least 90%, at least 95%, at least 96%, at least 97%, at least 98%, at least 99%, or 100% of sequence identity with each of amino acid sequences of SEQ ID NO: 11, 12, 13, and 14. A gene that encodes the lactate dehydrogenase may have at least 75%, at least 80%, at least 85%, at least 90%, at least 95%, at least 96%, at least 97%, at least 98%, at least 99%, or 100% of sequence identity with a nucleotide sequence of SEQ ID NO: 15.

The polynucleotide encoding LDH may be expressed from a vector including LDH derived from bacteria, yeast, fungus, or an animal such mammal, amphibian, or Sauropsida. The vector may include a replication origin, a promoter, a polynucleotide encoding a lactate dehydrogenase, and a terminator. The replication origin may include a yeast autonomous replication sequence (ARS). The yeast ARS may be stabilized by a yeast centrometric sequence (CEN). The promoter may be selected from the group consisting of a CYC promoter, a TEF promoter, a GPD promoter, and an ADH promoter. The CYC promoter, TEF promoter, GPD promoter, and ADH promoter may be, each respectively, have nucleotide sequences of SEQ ID NO: 17, 18, 19, and 20. The terminator may be selected from the group consisting of phosphoglycerate kinase 1 (PGK1), cytochrome c transcription (CYC1), and GAL1. The CYC1 terminator may have a nucleotide sequence of SEQ ID NO: 21. The vector may further include a selection marker.

The polynucleotide encoding LDH may be included in a genome of a yeast cell (e.g., a genetically engineered yeast cell). When the polynucleotide encoding LDH functions to produce active protein in a cell, the polynucleotide is deemed as "functional" in a cell. The polynucleotide encoding LDH is specific with respect to production of L-LDH or D-LDH, and thus a yeast cell including the polynucleotide encoding LDH may produce an L-lactate enantiomer, a D-lactate enantiomer, or a salt thereof.

The yeast cell may include one copy of a polynucleotide that encodes LDH or multiple copies of a polynucleotide that encodes LDH for example, 2 to 10 copies. The yeast cell may include 1 to 10, 1 to 8, 1 to 7, 1 to 6, 1 to 5, 1 to 4, 1, 2 to 10, 2 to 8, 2 to 7, 2 to 6, 2 to 5, 2 to 4, or 2 to 3 copies of LDH gene(s). When the yeast cell includes the polynucleotide encoding multiple LDHs, each of the polynucleotide may include copies of the same polynucleotide or copies of polynucleotides encoding at least two different LDHs. The multiple copies of the polynucleotide encoding exogenous LDHs may be included in the same locus or multiple loci in a genome of a host cell.

Moreover, the yeast cell may be *Saccharomyces cerevisiae*, in which activities of a polypeptide converting pyruvate to acetaldehyde, a polypeptide converting lactate to pyruvate, a polypeptide converting dihydroxyacetone phosphate (DHAP) to glycerol-3-phosphate (G3P), or a combination thereof are inactivated or decreased, and an activity of a polypeptide converting pyruvate to lactate is increased. Also, in the yeast cell, an activity of a polypeptide that catalyzes converting G3P to glycerol (e.g., GPP1 and GPP2), a polypeptide that catalyzes converting acetaldehyde to ethanol (e.g., ADH), or a combination thereof may be inactivated or decreased. *Saccharomyces cerevisiae* may be a KCTC 12415BP strain engineered as described herein.

The yeast cell is capable of producing lactate and may further include a polypeptide that has an activity of converting lactate to another product.

Also, the yeast cell may be *Saccharomyces cerevisiae*, in which an activity of an external mitochondrial NADH dehydrogenase is inactivated or decreased, activities of a polypeptide converting pyruvate to acetaldehyde, a polypeptide converting lactate to pyruvate, a polypeptide converting DHAP to glycerol-3-phosphate, or a combination thereof may be inactivated or decreased, and an activity of a polypeptide converting pyruvate to lactate may be increased.

According to another aspect of the present disclosure, provided is a method of producing lactate, wherein the method includes culturing the yeast cell described above; and collecting lactate from a culture.

According to another aspect of the present disclosure, provided is a method for producing a lactate-derived product, wherein the method includes culturing a yeast cell capable of producing lactate in which an activity of an external mitochondrial NADH dehydrogenase is inactivated or decreased, which further includes a polypeptide that converts the lactate to another product; and collecting a product from the culture.

The culturing of the yeast cell may be, for example, performed in a medium containing a carbon source, such as glucose. The medium used in the culturing of the yeast cell may be any conventional medium appropriate for growth of a yeast cell, such as a minimum or complex medium containing an appropriate supplement used in the cultivation of a yeast.

The medium used in the culturing may be a medium that may satisfy growth conditions of a particular yeast cell. The medium may include one selected from carbon source, nitrogen source, salts, trace elements, and a combination thereof.

Culture conditions may be appropriately controlled for the yeast cell, for example, a genetically modified yeast cell to produce lactate. The yeast cell may be cultured under an aerobic condition for its proliferation. Then, the yeast cell may be cultured under an anaerobic or microaerobic condition to produce lactate. The anaerobic or microaerobic condition may include a dissolved oxygen (DO) concentration of about 0% to about 10%, for example, about 0% to about 8%, about 0% to about 6%, about 0% to about 4%, or about 0% to about 2%. The expression "microaerobic condition" refers to a state in which the oxygen concentration in the culture medium is lower than that obtained when the culture medium is contacted with the normal atmospheric air. For example, a low level of oxygen can be less than about 10%, 5%, 1%, 0.1%, or 0.01%, about 0.01% to about 10%, about 0.01% to about 5%, about 0.01% to about 1%, about 0.01% to about 0.1%, about 0.1% to about 10%, about 1% to about 9%, about 2% to about 8%, about 3% or 7%, or about 4% to about 6% of the oxygen level in the culture medium obtained when the culture medium allowed to be contacted with the normal atmospheric air.

As used herein, the term "culture condition" denotes a condition for culturing a yeast cell. The culture condition may be, for example, a carbon source, nitrogen source, or oxygen condition for the yeast cell. The carbon source that is used by the yeast cell includes monosaccharides, disaccharides, or polysaccharides. The carbon source may be assimilable sugars. The assimilable sugars may include hexoses and pentoses. In particular, the carbon source may be glucose, fructose, mannose, or galactose. The nitrogen source that is used by the yeast cell may be an organic nitrogen compound or an inorganic nitrogen compound. In particular, amino acid, amide, amine, nitrate, or ammonium salt may be used. An oxygen condition for culturing yeast cell may be an aerobic condition of a normal oxygen partial pressure, a low-oxygen condition including about 0.1% to about 10%, for example, about 0.1% to about 8%, about 0.1% to about 6%, about 0.1% to about 4%, about 0.1% to about 2%, about 0.1% to about 1%, about 1% to about 10%, about 1% to about 8%, about 1% to about 6%, about 2% to about 10%, about 4% to about 10%, about 6% to about 10%, about 8% to about 10%, about 2% to about 8%, or about 2% to about 6%, of oxygen in the atmosphere, or an anaerobic condition including no oxygen. A metabolic pathway may be modified in accordance with a carbon source or nitrogen that may be actually used by a yeast cell.

The collecting may include separating the lactate from the culture. Separation of lactate from the culture may be performed by a separation method commonly known in the art. The separation method may be centrifugation, filtration, ion-exchange chromatography, or crystallization. For example, a supernatant obtained by centrifuging the culture at a low speed and removing a biomass may be separated through ion-exchange chromatography.

The present disclosure will be described in further detail with reference to the following examples. These examples are for illustrative purposes only and are not intended to limit the scope of the present disclosure.

Example 1

Preparation of Strain for Highly-Efficient Production of Lactate and Preparation of Expression Vector Saccharomyces cerevisiae CEN.PK2-1D (MATα ura3-52; trp1-289; leu2-3,112; his3 Δ 1; MAL2-8$^C$; SUC2, EUROSCARF accession number: 30000B) was used as a lactate production strain, and in order to block a production pathway of ethanol and glycerol as main byproducts, a pyruvate decarboxylase (pdc1) gene, which is a main enzyme of alcohol fermentation, a NAD-dependent glycerol-3-phosphate dehydrogenase (gpd1) gene, which is a main enzyme of glycerol biosynthesis, and a L-lactate cytochrome-c oxidoreductase2 (cyb2) gene, which is a lactate lyase, were inactivated by homologous recombination.

(1.1) Preparation of a L-LDH Overexpression Vector and Inactivation Vectors for pdc1, gpd1, and cyb2 Genes (1.1.1) Preparation of a L-LDH Overexpression Vector A CCW12 promoter PCR fragment obtained by performing PCR with a genomic DNA of Saccharomyces cerevisiae CEN.PK2-1D as a template and using primers of SEQ ID NO: 22 and SEQ ID NO: 23 was digested with SacI and XbaI, and the resultant was inserted into p416-GPD vector (ATCC 87360™) digested with SacI and XbaI, producing p416-CCW12p vector.

Then, L-ldh gene (SEQ ID NO: 11) was amplified from Pelodiscus sinensis japonicus genomic DNA by PCR using primers of SEQ ID NO: 24 and SEQ ID NO: 25. The resulting L-ldh PCR fragment and p416-CCW12p obtained therefrom were digested with BamHI and SalI, and ligated to each other, producing p416-CCW12p-LDH, which is an L-ldh expression vector.

The L-ldh expression vector included a yeast autonomous replication sequence (ARS)/a yeast centromeric sequence (CEN) of SEQ ID NO: 16 and a CYC1 terminator of SEQ ID NO: 21. Also, the CCW12 promoter may replaced with a CYC promoter of SEQ ID NO: 17, a TEF promoter of SEQ ID NO: 18, a GPD promoter of SEQ ID NO: 19, or an ADH promoter of SEQ ID NO: 20.

Figure 2:
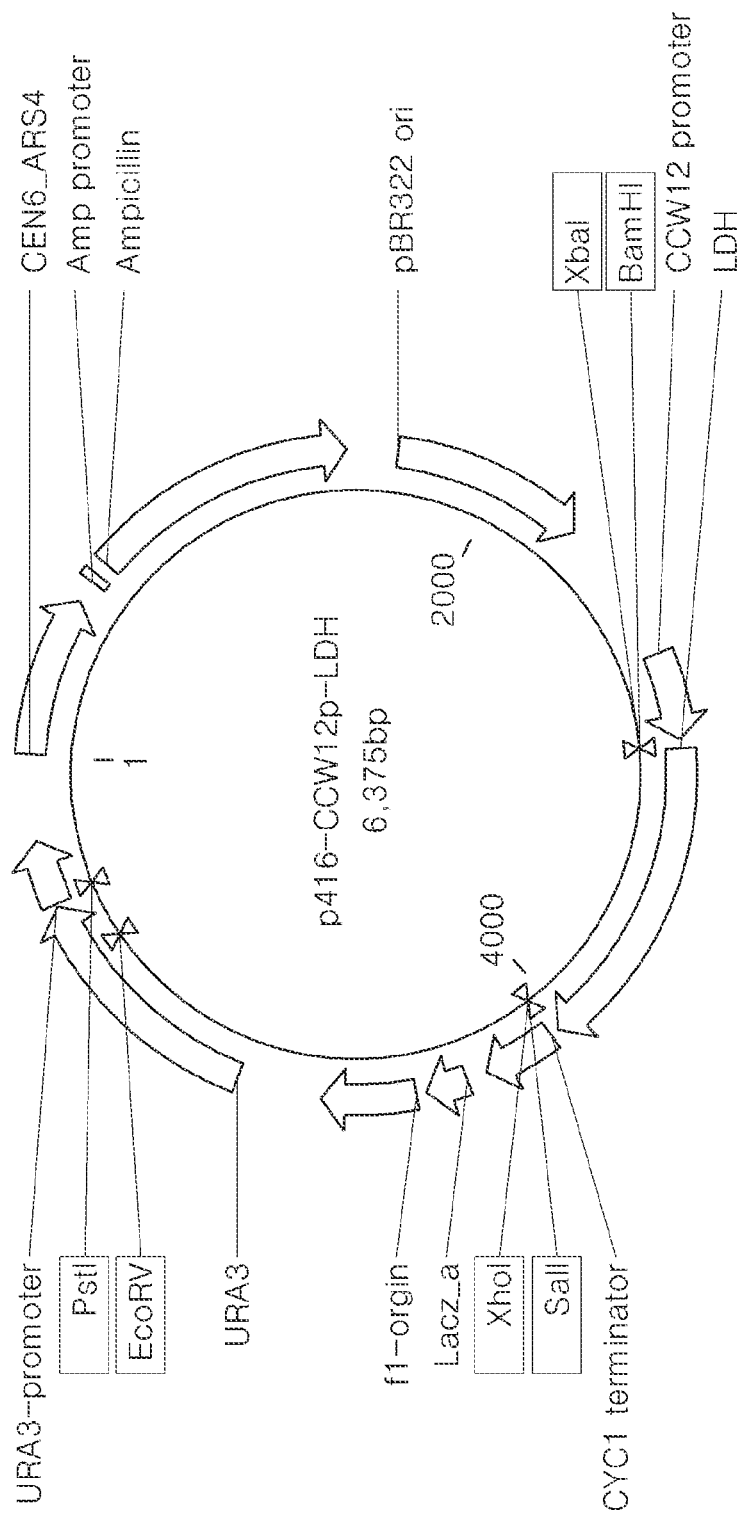
FIG. 2 is a vector map illustrating a p416-CCW12p-LDH vector.

FIG. 2 is a view illustrating a p416-CCW12p-LDH vector. As shown in FIG. 2, the LDH derived from Pelodiscus sinensis japonicus was introduced into the vector.

(1.1.2) Preparation of a Gene Exchange Vector

Figure 3:
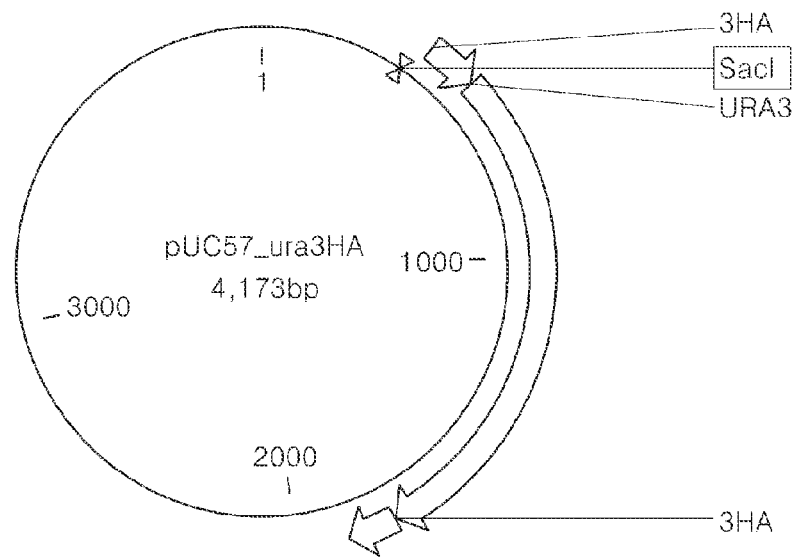
FIG. 3 is a vector map illustrating a pUC57-ura3HA vector.
Figure 4:
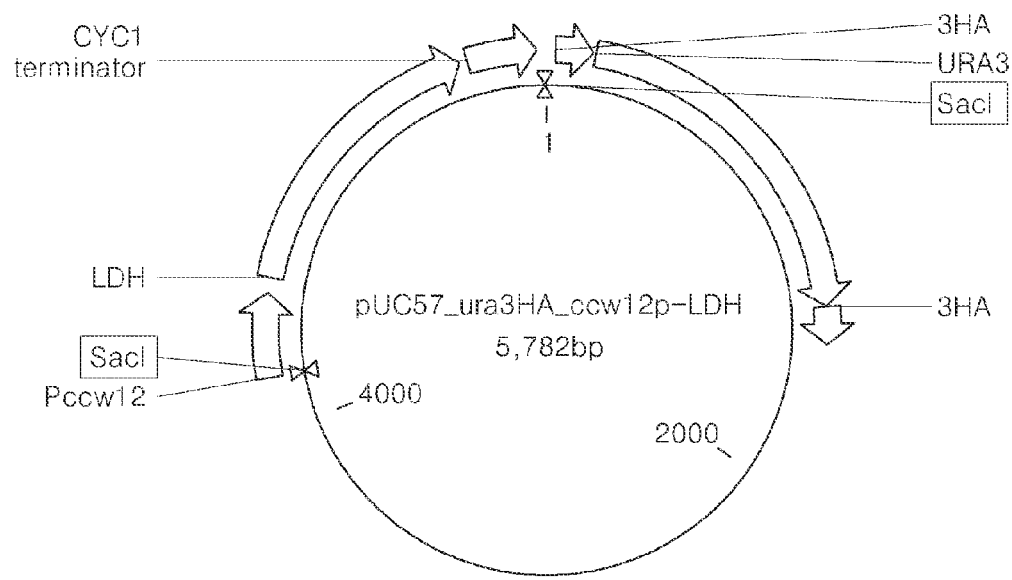
FIG. 4 is a vector map illustrating a pUC57-ura3HA-CCW12p-LDH vector.

PDC1, CYB2, and GPD1 genes were deleted by using a homologous recombination method, and at the same time, a gene exchange vector for introducing a L-LDH gene was prepared in the same manner described below. FIG. 3 illustrates a pUC57-ura3HA (SEQ ID NO: 52) vector. 3HA represents three repeats of the HA (haemagglutinin) gene. FIG. 4 illustrates a pUC57-ura3HA-CCW12p-LDH vector.

PCR was performed using the prepared p416-CCW12p-LDH as a template with primers of SEQ ID NOS: 26 and 27. The resulting PCR fragment and the prepared pUC57-ura3HA vector were digested with SacI and ligated to each other, producing pUC57-ura3HA-CCW12p-LDH.

PCR was performed using the prepared pUC57-ura3HA-CCW12p-LDH as a template with primers of SEQ ID NOS: 28 and 29, thereby producing a PDC1 gene deletion cassette.

PCR was performed using the prepared pUC57-ura3HA-CCW12p-LDH as a template with primers of SEQ ID NOS: 30 and 31, producing a CYB2 gene deletion cassette.

PCR was performed using the prepared pUC57-ura3HA-CCW12p-LDH as a template with primers of SEQ ID NOS: 32 and 33, producing a GPD1 gene deletion cassette.

(1.2) Inactivation of pdc1, cyb2, and gpd1 Genes

A mutant strain of Saccharomyces cerevisiae CEN.PK2-1D, in which pdc1 is deleted, was prepared as follows. Saccharomyces cerevisiae CEN.PK2-1D was plated onto a YPD agar plate (including 10 g/L of yeast extract, 20 g/L of peptone, 20 g/L of glucose, and 20 g/L agar) and incubated for 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C. After about 4 to 5 hours, when the optical density at 600 nm ($OD_{600}$) reached about 0.5, the culture was centrifuged at a rate of about 4,500 rpm for about 10 minutes to harvest cells, and the cells were resuspended in about 100 mM lithium acetate solution. Then, the cells were harvested by performing centrifugation at a rate of about 4,500 rpm for about 10 minutes, resuspended in about 1M lithium acetate solution containing about 15 (v/v) % glycerol, and then divided into a volume of about 100 ul each.

In order to delete a pdc1 gene, the PDC1 deletion cassette prepared in Example 1.1.2 was mixed with 50% of polyethyleneglycol and a single stranded carrier DNA and reacted in a water bath for about 1 hour at 42° C., and then, the culture solution was spreaded on a uracil-free minimal agar plate YSD (Yeast Synthetic Drop-out) Medium, containing 6.7 g/L of yeast nitrogen base without amino acids (Sigma-Aldrich: Cat. no. Y0626), 1.4 g/L of Yeast synthetic drop-out without uracil (Sigma-Aldrich: Cat. no. Y1501), 20 g/L glucose, and 20 g/L of agar) and grown for about 24 hours or more at 30° C. Ten colonies (mutant strains) grown on the plate were selected, transferred onto the fresh uracil-free minimal agar plate, and at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of pdc1 gene, PCR was performed using the isolated genomic DNA of the mutant strain as a template with primers of SEQ ID NOS: 34 and 35, and then, electrophoresis was performed on the obtained PCR product to confirm deletion of pdc1 gene. As a result, *Saccharomyces cerevisiae* CEN.PK2-1D (Δ pdc1::Idh+ura3) was obtained.

Also, for additional gene deletion using the gene exchange vector, a selection marker URA3 gene, which was introduced for the preparation of a CEN.PK2-1D (Δ pdc1::Idh+ura3) strain, was removed from those strains. *Saccharomyces cerevisiae* CEN.PK2-1D (Δ pdc1::Idh+ura3) was inoculated in about 10 ml of a YPD liquid medium (10 g/L Yeast extract, 20 g/L peptone and 20 g/L glucose), cultured for about 18 hours at 30° C., and spread on a 5-FOA (5-fluoro-orotic acid) plate (YSD medium, containing 6.7 g/L of yeast nitrogen base without amino acids, 1.4 g/L of yeast synthetic drop-out, 20 g/L glucose, 1 μg/L of 5-fluoroorotic acid and 20 g/L of agar), and cultured for about 24 hours or more at 30° C. Ten colonies (a URA3 pop-out strain) grown on the 5-FOA plate were selected, patched onto the fresh 5-FOA plate, and, at the same time, cultured in a YPD liquid medium to isolate genomic DNA from the selected strain by using a commonly used kit (Gentra Puregene Cell kit, Qiagen, USA). In order to confirm deletion of URA3 gene, PCR was performed using the isolated genomic DNA of the URA3 pop-out strain as a template with primers of SEQ ID NOS: 34 and 35, and then electrophoresis was performed on the obtained PCR product to confirm deletion of URA3 gene. As a result, *Saccharomyces cerevisiae* CEN.PK2-1D (Δ pdc1::Idh) was obtained.

Deletion of cyb2 gene in *Saccharomyces cerevisiae* CEN.PK2-1D (Δpdc1::Idh) was prepared in the same manner as follows. *Saccharomyces cerevisiae* CEN.PK2-1D (Δpdc1::Idh) was plated onto a YPD agar plate (10 g/L of yeast extract, 20 g/L of peptone, 20 g/L of glucose, and 20 g/L agar) and incubated for 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C. After about 4 to 5 hours, when the $OD_{600}$ reached about 0.5, the culture was centrifuged at a rate of about 4,500 rpm for about 10 minutes to harvest cells, and the cells were resuspended in about 100 mM lithium acetate solution. Then, the cells were harvested by performing centrifugation at a rate of about 4,500 rpm for about 10 minutes, resuspended in about 1 M lithium acetate solution including about 15% of glycerol, and then divided into a volume of about 100 ul each.

In order to delete a cyb2 gene, a cyb2 deletion cassette, which is prepared in Examples 1 and 2 in the same manner as the pdc1 deletion cassette was prepared in Example 1.1.2, was mixed with 50% of polyethylene glycol and a single stranded carrier DNA and reacted in a water bath for about 1 hour at 42° C., and then, the culture solution was spread on a uracil-free minimal agar plate (YSD medium, containing 6.7 g/L of yeast nitrogen base without amino acids, 1.4 g/L of yeast synthetic drop-out without uracil, 20 g/L glucose, and 20 g/L of agar) and grown for about 24 hours or more at 30° C. Ten colonies (mutant strains) grown on the plate were selected, transferred onto the fresh uracil-free minimal agar plate, and at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of cyb2 gene, PCR was performed using the isolated genomic DNA of the mutant stain as a template with primers of SEQ ID NOS: 36 and 37, and then, electrophoresis was performed on the obtained PCR product to confirm deletion of cyb2 gene. As a result, *Saccharomyces cerevisiae* CEN.PK2-1D (Δ pdc1::Idh Δ cyb2::Idh+ura3) was obtained.

Also, for additional gene deletion using the gene exchange vector, a selection marker URA3 gene was removed from those strains by using the URA3 pop-out method as described above. *Saccharomyces cerevisiae* CEN.PK2-1D (Δpdc1::Idh Δcyb2::Idh+ura3) was inoculated in about 10 ml of a YPD liquid medium, cultured for about 18 hours at 30° C., and spread on a 5-FOA plate (YSD, containing 6.7 g/L of yeast nitrogen base without amino acids, 1.4 g/L of yeast synthetic drop-out, 20 g/L glucose, 1 μg/L of 5-fluoroorotic acid, and 20 g/L agar), and cultured for about 24 hours or more at 30° C. Ten colonies (a URA3 pop-out strain) grown on the 5-FOA plate were selected, transferred onto the fresh 5-FOA plate, and, at the same time, cultured in a YPD liquid medium to isolate genomic DNA from the selected strain by using a commonly used kit (Gentra Puregene Cell kit, Qiagen, USA). In order to confirm deletion of URA3 gene, PCR was performed using the isolated genomic DNA of the URA3 pop-out strain as a template with primers of SEQ ID NOS: 36 and 37, and then electrophoresis was performed on the obtained PCR product to confirm deletion of URA3 gene. As a result, *Saccharomyces cerevisiae* CEN.PK2-1D (Δpdc1::Idh Δcyb2::Idh) was obtained.

Deletion of gpd1 gene in *Saccharomyces cerevisiae* CEN.PK2-1D (Δ pdc1::IdhΔcyb2::Idh) was prepared in the same manner as follows. *Saccharomyces cerevisiae* CEN.PK2-1D (Δpdc1::IdhΔcyb2::Idh) was plated onto a YPD agar plate (10 g/L of yeast extract, 20 g/L of peptone, 20 g/L of glucose, and 20 g/L agar) and incubated for about 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and at about 30° C. After about 4 to 5 hours, when the $OD_{600}$ reached about 0.5, the culture was centrifuged at a rate of about 4,500 rpm for about 10 minutes to harvest cells, and the cells were resuspended in about 100 mM lithium acetate solution. Then, the cells were harvested by performing centrifugation at a rate of about 4,500 rpm for about 10 minutes, resuspended in about 1M lithium acetate solution including about 15% of glycerol, and then divided into a volume of about 100 ul each.

In order to delete a gpd1 gene, a gpd1 deletion cassette, which is prepared in Example 1.2 in the same manner as the pdc1 deletion cassette and the cyb2 deletion cassette were prepared, was mixed with 50% of polyethyleneglycol and a single stranded carrier DNA and reacted in a water bath for about 1 hour at 42° C., and then, the culture solution was spread on a uracil-free minimal agar plate (YSD, containing 6.7 g/L of yeast nitrogen base without amino acids, 1.4 g/L of yeast synthetic drop-out without uracil, 20 g/L glucose, and 20 g/L of agar) and grown for 24 hours or more at 30° C. Ten colonies (mutant strains) grown on the plate were selected, transferred onto the fresh uracil-free minimal agar plate, and, at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of gpd1, PCR was performed using the isolated genomic DNA of the mutant strain as a template with primers of SEQ ID NOS: 38 and 39, and then, electrophoresis was performed on the obtained PCR product to confirm deletion of gpd1 gene. As a result, *Saccharomyces cerevisiae* CEN.PK2-1D (Δ pdc1::Idh Δ cyb2::Idh Δ gpd1::Idh+ura3) was obtained.

Also, for additional gene deletion using the gene exchange vector, a selection marker URA3 gene was removed from those strains by using the URA3 pop-out method as described above. *Saccharomyces cerevisiae* CEN.PK2-1D (Δ pdc1::Idh Δcyb2::Idh Δ gpd1::Idh+ura3) was inoculated in about 10 ml of a YPD liquid medium, cultured for about 18 hours at 30° C., spread on a 5-FOA plate (YSD, containing 6.7 g/L of yeast nitrogen base without amino acids, 1.4 g/L of yeast synthetic drop-out, 20 g/L glucose, 1 µg/L of 5-fluoroorotic acid, and 20 g/L agar), and cultured for about 24 hours or more at 30° C. Ten colonies (URA3 pop-out strains) grown on the 5-FOA plate were selected, transferred onto the fresh 5-FOA plate, and, at the same time, cultured in a YPD liquid to isolate the genomic DNA from the above mutant strains by using a commonly used kit (Gentra Puregene Cell kit, Qiagen, USA). In order to confirm deletion of URA3 gene, PCR was performed using the isolated genomic DNA of the URA3 pop-out strain as a template with primers of SEQ ID NOS: 38 and 39, and then electrophoresis was performed on the obtained PCR product to confirm URA3 deletion. As a result, *Saccharomyces cerevisiae* CEN.PK2-1D (Δ pdc1::Idh Δcyb2::Idh Δ gpd1::Idh) was obtained.

*Saccharomyces cerevisiae* CEN.PK2-1D (Δ pdc1::Idh Δ cyb2::Idh Δgpd1::Idh) was deposited in Korean Collection for Type Cultures (KCTC) on May 30, 2013, and received an accession number KCTC 12415BP.

(1.3) LDH Enhancement

An additional modification, such as redox balance enhancement, for increasing lactate production may be performed on KCTC 12415BP or L-Idh may be additionally introduced to genome for enhancement of a lactate production pathway as follows.

(1.3.1) Preparation of Introduction Vector for L-Idh Gene into a Genome

Figure 5:
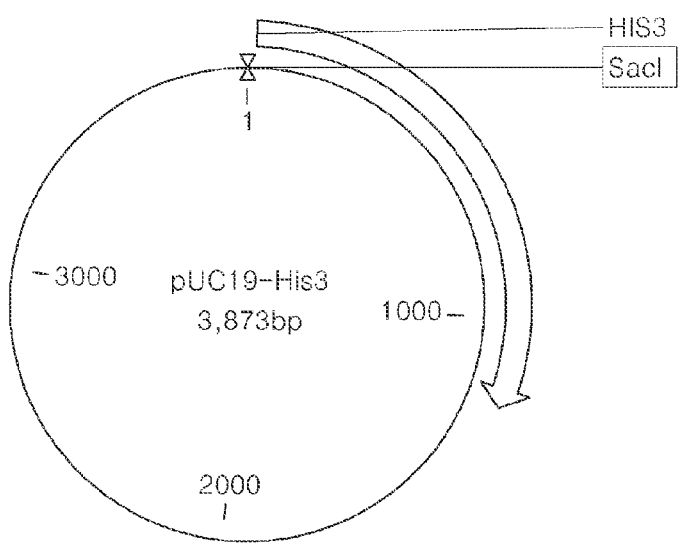
FIG. 5 is a vector map illustrating a pUC19-HIS3 vector.
Figure 6:
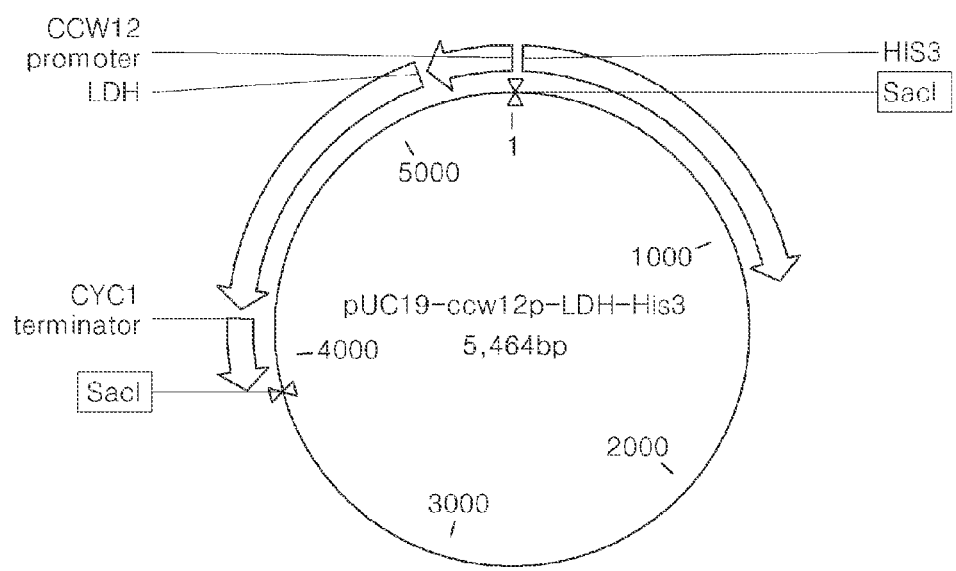
FIG. 6 is a vector map illustrating a pUC19-CCW12p-LDH-His3 vector.

A gene introduction vector for additional introduction of L-Idh was prepared as follows. FIG. 5 illustrates a pUC19-HIS3 vector (SEQ ID NO: 53). A HIS3 PCR fragment obtained by performing PCR with pRS413 (ATCC8758) vector as a template and using primers of SEQ ID NO: 54 and SEQ ID NO: 55 was digested with SalI, and the resultant was inserted into pUC19 vector (NEB, N3041) digested with SalI, producing pUC19-HIS3 vector.), which may be used as a selection marker for a HIS3 gene. FIG. 6 illustrates a pUC19-CCW12p-LDH-HIS3 vector.

PCR was performed using the prepared p416-CCW12p-LDH as a template and primers of SEQ ID NOS: 26 and 27. The resulting PCR fragment and the prepared pUC19-HIS3 vector were digested with SacI, and the resultant fragments were ligated to each other, producing pUC19-CCW12p-LDH-HIS3.

Also, in order to additionally introduce L-Idh into a genome of a strain of KCTC 12415BP, PCR was performed by using the prepared pUC19-CCW12p-LDH-HIS3 as a template and primers of SEQ ID NOS: 40 and 41, and thus a cassette to be inserted in a location of TRP1 (phosphoribosyl-anthranilate isomerase) gene was prepared.

The cassette including L-Idh may be inserted to a TRP1 gene, and in this case, L-Idh may be inserted as the TRP1 gene is deleted. A L-Idh inserted strain may be prepared as follows.

A strain of KCTC 12415BP was plated onto a YPD agar plate (10 g/L of yeast extract, 20 g/L of peptone, 20 g/L of glucose, and 20 g/L of agar) and cultured for about 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and a temperature of about 30° C.

After about 4 to 5 hours, when $OD_{600}$ was about 0.5, the culture was centrifuged at a rate of about 4,500 rpm for about 10 minutes to obtain cells, and the cells were resuspended in a lithium acetate solution at a concentration of about 100 mM. Then, the cells were obtained by performing centrifugation at a rate of about 4,500 rpm for about 10 minutes, resuspended in a lithium acetate solution at a concentration of about 1 M including about 15% of glycerol, and then divided into a volume of about 100 ul each.

In order to delete a TRP1 gene and simultaneously express L-Idh, a L-Idh expression cassette, which is prepared in Example 1.3.1 and includes a HIS3 gene as a selection marker, was mixed with 50% of polyethylene glycol and a single stranded carrier DNA and reacted in a water bath for about 1 hour at 42° C., and then, the culture solution was plated onto a histidine (his)-free minimal agar plate (YSD, containing 6.7 g/L of yeast nitrogen base without amino acids, 1.4 g/L of yeast synthetic drop-out without histidine (Sigma-Aldrich: Cat. no. Y1751), 20 g/L glucose, and 20 g/L of agar) and cultured for 24 hours or more at 30. Ten colonies (mutant strains) grown on the plate were selected, transferred onto the fresh YSD (-his) agar plate, and, at the same time, cultured in a YSD (-his) liquid medium to isolate the genomic DNA from the above mutant strains by using a commonly used kit (Gentra Puregene Cell kit, Qiagen, USA). PCR was performed by using the isolated genomic DNA of the mutant strain as a template and primers of SEQ ID NOS: 42 and 43, and then, electrophoresis was performed on the obtained PCR product to confirm insertion of the L-Idh expression cassette. As a result, the obtained strain was referred to as CEN.PK2-1D KCTC12415BP Δ trp1::Idh.

Example 2

Preparation of nde1 Gene Deletion Cassette and Preparation of *Saccharomyces cerevisiae* Strain from which nde1 is Deleted (2.1) Preparation of nde1 Gene Deletion Cassette In order to delete an nde1 gene by using a homologous recombination method, a vector for inactivating the nde1 gene is prepared using pUC57-ura3HA prepared in Example 1.1.2. PCR was performed by using the prepared pUC57-ura3HA as a template and primers of SEQ ID NOS: 44 and 45, producing an nde1 gene deletion cassette.

(2.2) Preparation of *Saccharomyces cerevisiae* Strain from which nde1 is Deleted Deletion of nde1 gene in *Saccharomyces cerevisiae* CEN.PK2-1D (KCTC12415BP Δ trp1::Idh) was prepared in the same manner as follows. *Saccharomyces cerevisiae* CEN.PK2-1D (KCTC12415BP Δ trp1::Idh) was spreaded on a YPD agar plate (10 g/L of yeast extract, 20 g/L of peptone, 20 g/L of glucose, and 20 g/L of agar) and cultured for about 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and a temperature of about 30° C. After about 4 to 5 hours, when $OD_{600}$ was about 0.5, the culture was centrifuged at a rate of about 4,500 rpm for about 10 minutes to obtain cells, and the cells were resuspended in a lithium acetate solution at a concentration of about 100 mM. Then, the cells were obtained by performing centrifugation at a rate of about 4,500 rpm for about 10 minutes, resuspended in a lithium acetate solution at a concentration of about 1 M including about 15% of glycerol, and then divided into a volume of about 100 ul each.

In order to remove an nde1 gene, an nde1 gene deletion cassette, which is prepared in Example 2.1 in the same manner as to delete pdc1, cyb2, and gpd1, was mixed with 50% of polyethyleneglycol and a single stranded carrier DNA and reacted in a water bath for about 1 hour at about 42° C., and then, the culture solution was spread on a uracil-free minimal agar plate (YSD, containing 6.7 g/L of yeast nitrogen base without amino acids, 1.4 g/L of yeast synthetic drop-out without uracil, 20 g/L glucose, and 20 g/L of agar) in a plate and cultured for 24 hours or more at about 30° C. Ten colonies (mutant strains) grown on the uracil-free minimal agar plate were selected, transferred onto the fresh uracil-free minimal agar plate, and, at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of the nde1 gene, PCR was performed using the isolated genomic DNA of the mutant strain as a template with primers of SEQ ID NOS: 46 and 47, and then, electrophoresis was performed on the obtained PCR product to confirm deletion of ned1 gene. As a result, *Saccharomyces cerevisiae* CEN.PK2-1D (KCTC12415BP Δ trp1::Idh Δ nde1+ura3) was obtained.

Also, for additional gene deletion using the gene exchange vector, a selection marker URA3 gene was removed from those strains by using the URA3 pop-out method as described above. *Saccharomyces cerevisiae* CEN.PK2-1D (KCTC12415BP Δ trp1::Idh Δ nde1+ura3) was inoculated in about 10 ml of a YPD liquid medium, cultured for about 18 hours at about 30° C., spread on a 5-FOA plate (YSD, containing 6.7 g/L of yeast nitrogen base without amino acids, 1.4 g/L of yeast synthetic drop-out, 20 g/L glucose, 1 μg/L of 5-fluoroorotic acid, and 20 g/L agar), and cultured for about 24 hours or more at a 30° C. Ten colonies (URA3 pop-out strains) grown on the 5-FOA plate were selected, transferred onto the fresh 5-FOA plate, and, at the same time, cultured in a YPD liquid to isolate the genomic DNA from the above mutant strains by using a commonly used kit (Gentra Puregene Cell kit, Qiagen, USA). In order to confirm deletion of URA3 gene, PCR was performed using the isolated genomic DNA of the URA3 pop-out strain as a template with primers of SEQ ID NOS: 46 and 47, and then electrophoresis was performed on the obtained PCR product to confirm deletion of URA3 gene. As a result, *Saccharomyces cerevisiae* CEN.PK2-1D (KCTC12415BP Δ trp1::Idh Δ nde1) was obtained.

Example 3

Preparation of nde2 Gene Deletion Cassette and Preparation of *Saccharomyces cerevisiae* Strain from which nde1 and nde2 are Deleted (3.1) Preparation of nde2 Gene Deletion Cassette A vector for inactivating an nde2 gene is pUC57-ura3HA prepared in Example 1.1.2. In order to prepare a nde2 gene deletion cassette, PCR was performed using the prepared pUC57-ura3HA as a template and primers of SEQ ID NOS: 48 and 49.

(3.2) Preparation of *S. cerevisiae* Strain from which nde1 and nde2 are Deleted Deletion of nde2 gene in *Saccharomyces cerevisiae* CEN.PK2-1D (KCTC12415BP Δ trp1::Idh Δ nde1) was prepared in the same manner as follows.

*Saccharomyces cerevisiae* CEN.PK2-1D (KCTC12415BP Δ trp1::Idh Δ nde1) was plated onto a YPD agar plate (10 g/L of yeast extract, 20 g/L of peptone, 20 g/L of glucose, and 20 g/L of agar) and cultured for about 24 hours at about 30° C., and then, a colony obtained therefrom was inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of 1% (v/v) and cultured in an incubator at a rate of about 230 rpm and a temperature of about 30° C. After about 4 to 5 hours, when $OD_{600}$ was about 0.5, the culture was centrifuged at a rate of about 4,500 rpm for about 10 minutes to obtain cells, and the cells were resuspended in a lithium acetate solution at a concentration of about 100 mM. Then, the cells were obtained by performing centrifugation at a rate of about 4,500 rpm for about 10 minutes, resuspended in a lithium acetate solution at a concentration of about 1 M including about 15% of glycerol, and then divided into a volume of about 100 ul each.

In order to remove a nde2 gene, a nde2 gene deletion cassette, which was prepared in Example 3.1 in the same manner in deletion of pdc1, cyb2, gpd1, and nde1 genes, was mixed with 50% of polyethylene glycol and a single stranded carrier DNA and reacted in a water bath for about 1 hour at about 42° C., and then, the culture solution was spread on a uracil-free minimal agar plate (YSD, containing 6.7 g/L of yeast nitrogen base without amino acids, 1.4 g/L of yeast synthetic drop-out without uracil, 20 g/L glucose, and 20 g/L of agar) and cultured for 24 hours or more at about 30° C. Ten colonies (mutant strains) grown on the uracil-free minimal agar plate were selected, transferred onto the fresh uracil-free minimal agar plate, and, at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of nde2 gene, PCR was performed using the isolated genomic DNA of the mutant strain as a template with primers of SEQ ID NOS: 50 and 51, and then, electrophoresis was performed on the obtained PCR product to confirm deletion of ned2 gene. As a result, *Saccharomyces cerevisiae* CEN.PK2-1D (KCTC12415BP Δ trp1::Idh Δ nde1Δnde2+ura3) was obtained.

Also, for additional gene deletion using the gene deletion vector, a selection marker URA3 gene was removed from those strains by using the URA3 pop-out method as described above. *Saccharomyces cerevisiae* CEN.PK2-1D (KCTC12415BP Δ trp1::Idh Δ nde1Δnde2+ura3) was inoculated in about 10 ml of a YPD liquid medium, cultured for about 18 hours at about 30° C., spread on a 5-FOA plate (YSD, containing 6.7 g/L of yeast nitrogen base without amino acids, 1.4 g/L of yeast synthetic drop-out, 20 g/L glucose, 1 μg/L of 5-fluoroorotic acid, and 20 g/L of agar), and cultured for about 24 hours or more at 30° C. Ten colonies (URA3 pop-out strains) grown on the 5-FOA plate were selected, transferred onto the fresh 5-FOA plate, and, at the same time, cultured in a YPD liquid to isolate the genomic DNA from the above mutant strains by using a commonly used kit (Gentra Puregene Cell kit, Qiagen, USA). In order to confirm deletion of URA3 gene, PCR was performed using the isolated genomic DNA of the URA3 pop-out strain as a template with primers of SEQ ID NOS: 50 and 51, and then electrophoresis was performed on the obtained PCR product to confirm deletion of URA3 gene. As a result, *Saccharomyces cerevisiae* CEN.PK2-1D (KCTC12415BP Δ trp1::Idh Δ nde1Δnde2) was obtained.

Example 4

Lactate Production Using Each of a Strain in which Nde1 is Inactivated and a Strain in which nde1 and nde2 are Inactivated The strains each respectively prepared in Examples 2 and 3 are plated onto a YPD agar plate and cultured for about 24 hours at about 30° C., and then, inoculated in about 50 ml of a YPD liquid medium including 40 g/L of glucose and cultured for about 16 hours at about 30° C. An amount of the culture that has a cell concentration of 5.0 at a light absorbance of 600 nm in the 50 ml of the culture medium as measured by using a spectrophotometer was quantified, centrifuged, and the supernatant is removed. Then, the cell was resuspended, inoculated in 50 ml of a new YPD liquid medium including 80 g/L of glucose, and then fermented.

The cell was cultured in a flask that maintains conditions for the fermentation at a rate of about 90 rpm and a temperature of 30° C. for about 24 hours or more in a microaerobic conditions, i.e., in the conditions of stirring the flask while the inlet thereof is closed with plug. Samples were periodically obtained from the flask during the fermentation, and the obtained samples were centrifuged at a rate of 13,000 rpm for about 10 minutes, and then metabolites of the supernatant and concentrations of lactate and glucose were analyzed by using a high-pressure liquid chromatography (HPLC).

As shown in Table 1, a productivity of KCTC12415BPΔtrp1::Idh Δ nde1 increased from 32.8 g/L to 34.4 g/L compared to KCTC12415BPΔtrp1::Idh. Also, a productivity of KCTC12415BP Δ trp1::Idh Δ nde1Δnde2 increased from 32.8 g/L to 37.7 g/L, and a yield of KCTC12415BP Δ trp1::Idh Δ nde1Δnde2 increased from 44.2% to 48.2% compared to KCTC12415BPΔtrp1::Idh.

TABLE 1

| Strain | $OD_{600}$ | Productivity of L-lactate (g/L) | Yield (%) |
|---|---|---|---|
| KCTC12415BPΔtrp1::ldh | 11.74 | 32.8 | 44.2 |
| KCTC12415BPΔtrp1::ldh Δ nde1 | 12.78 | 34.4 | 44.2 |
| KCTC12415BP Δ trp1::ldh Δ nde1 Δ nde2 | 11.64 | 37.7 | 48.2 |

Cultured for about 30 hours in a 50 ml flask.

Example 5

Production of Lactate Using KCTC12415BPΔtrp1::Idh Δ nde1 Strain

The KCTC12415BPΔtrp1::Idh Δ nde1 strain prepared in Example 2 was plated onto a YPD agar plate and cultured for about 24 hours or more at about 30° C., and then a colony obtained thereform was inoculated in 100 ml YPD including 80 g/L of glucose and cultured for about 16 hours at about 30° C. in an aerobic condition.

100 ml of the strain culture was separately inoculated in a microbioreactor containing 1 L of a synthetic medium (60 g/L of glucose, 20 g/L of a yeast extract, 50 g/L of $K_2HPO_4$, 10 g/L of $MgSO_4$, 0.1 g/L of tryptophane, and 0.1 g/L of histidine) and fermented, and fermentation conditions were maintained at initial concentrations of 60 g/L of glucose and 20 g/L of a yeast extract at 30° C. During the fermentation, pH was maintained at about pH 5 up to 16 hours, pH 4.5 up to 24 hours, and at 3.0 up to 60 hours by using 5 N $Ca(OH)_2$, and a concentration of the glucose was maintained at 20 g/L. Additional synthesis medium components include 50 g/L of $K_2HPO_4$, 10 g/L of $MgSO_4$, 0.1 g/L of tryptophane, and 0.1 g/L of histidine in addition to the glucose.

A cell concentration in the culture solution was measured by using a spectrophotometer. During the fermentation, samples were obtained periodically from a bioreactor, and the obtained samples were centrifuged at a rate of 13,000 rpm for 10 minutes, and then metabolites of the supernatant and concentrations of lactate and glucose were analyzed by HPLC.

Figure 7:
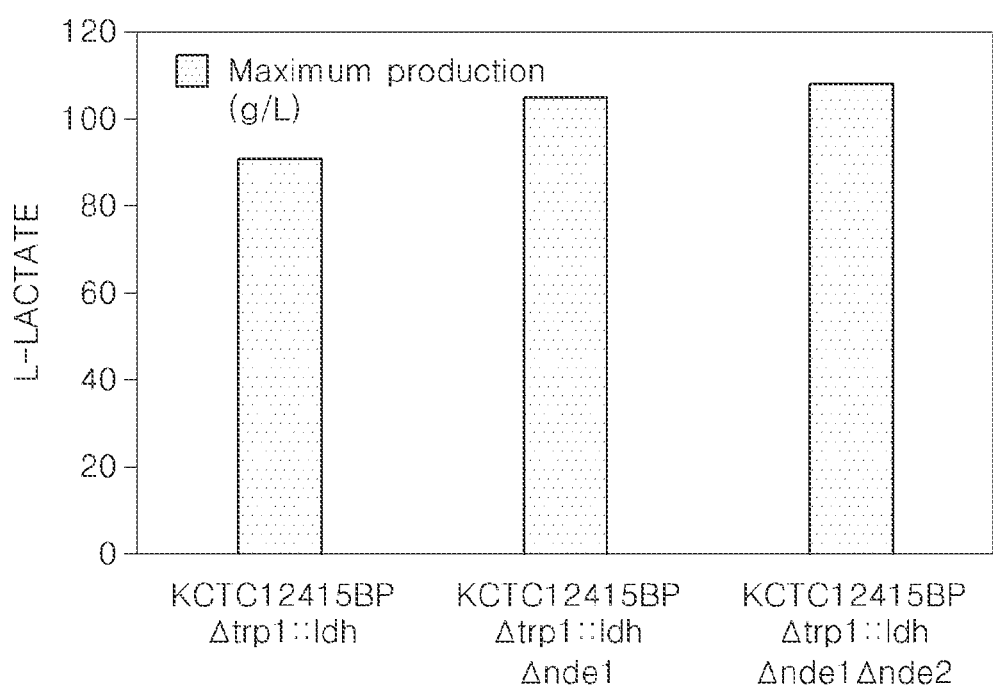
FIG. 7 is a bar graph showing productivity of lactate under fermentation conditions of KCTC12415BP+LDH, KCTC12415BP+LDH Δ NDE1 and KCTC12415BP+LDH Δ NDE1 Δ NDE2.

FIG. 7 illustrates lactate productivity under fermentation conditions of KCTC12415BPΔtrp1::Idh, KCTC12415BPΔtrp1::Idh Δ nde1 and KCTC12415BP Δ trp1::Idh Δ nde1Δnde2 according to an embodiment of the present invention. As shown in FIG. 7, a recombinant KCTC12415BPΔtrp1::Idh Δ nde1 strain may have excellent lactate productivity and a yield that is increased than that of a mother strain. The recombinant KCTC12415BPΔtrp1::Idh

Example 6

Production of Lactate Using KCTC12415BP Δ trp1::Idh Δ nde1Δnde2 Strain

The KCTC12415BP Δ trp1::Idh Δ nde1Δnde2 strain prepared in Example 3 was plated onto a YPD agar plate and cultured for about 24 hours or more at 30° C., and then a colony obtained therefrom was inoculated in 100 ml YPD including 80 g/L of glucose and cultured for about 16 hours at about 30° C. in an aerobic condition. 100 ml of the strain culture was separately inoculated in a microbioreactor containing 1 L of a synthetic medium (60 g/L of glucose, 20 g/L of a yeast extract, 50 g/L of $K_2HPO_4$, 10 g/L of $MgSO_4$, 0.1 g/L of tryptophane, and 0.1 g/L of histidine) and fermented.

Fermentation conditions were maintained at initial concentrations of 60 g/L of glucose and 20 g/L of a yeast extract at 30° C. During the fermentation, pH was maintained at about pH 5 up to 16 hours, pH 4.5 up to 24 hours, and at 3.0 up to 60 hours by using 5N $Ca(OH)_2$, and a concentration of the glucose was maintained at 20 g/L. Additional synthetic medium compositions include 50 g/L of $K_2HPO_4$, 10 g/L of $MgSO_4$, 0.1 g/L of tryptophane, and 0.1 g/L of histidine in addition to the glucose.

A cell concentration in the culture solution was measured by using a spectrophotometer. During the fermentation, samples were obtained periodically from a bioreactor, and the obtained samples were centrifuged at a rate of 13,000 rpm for 10 minutes, and then metabolites of the supernatant and concentrations of lactate and glucose were analyzed by HPLC.

As shown in FIG. 7, a recombinant KCTC12415BP Δ trp1::Idh Δ nde1Δnde2 strain may have an excellent lactate productivity and a yield that is increased than that of a mother strain. The recombinant KCTC12415BP Δ trp1::Idh Δ nde1Δnde2 strain has a lactate productivity that increased from 91 g/L to 111 g/L compared to the control group, KCTC12415BP Δ trp1::Idh.

Figure 8A:
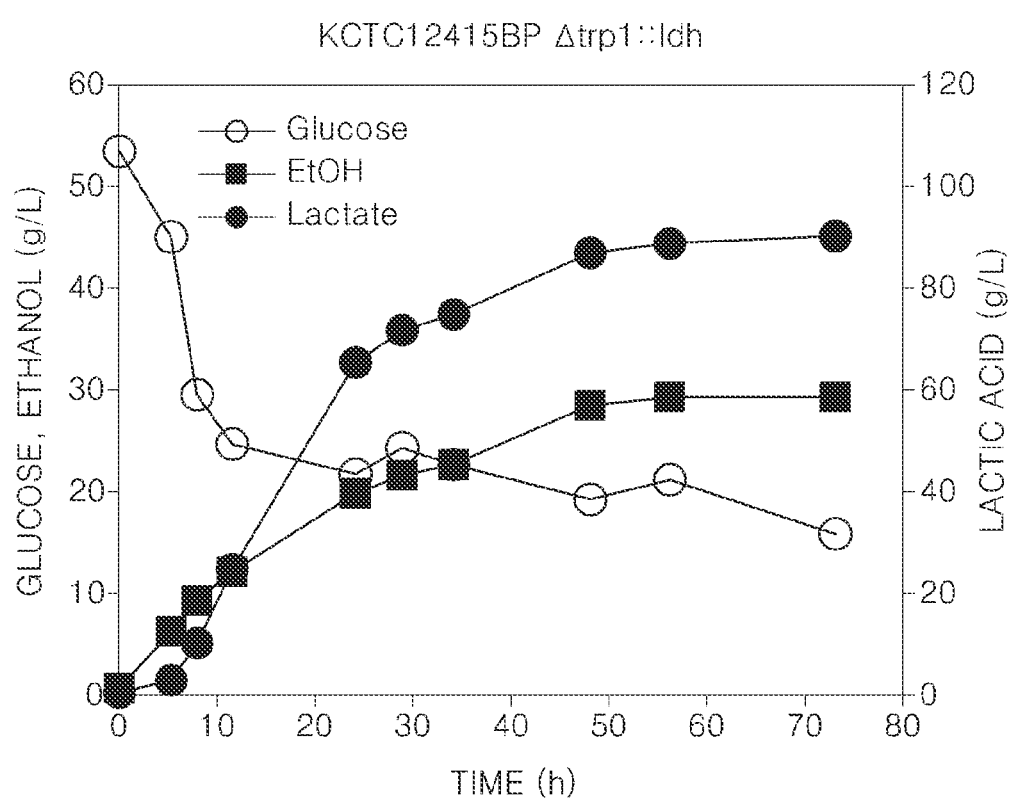
FIG. 8A is a graph illustrating culturing characteristics of KCTC12415BPΔtrp1::Idh under fermentation conditions.
Figure 8B:
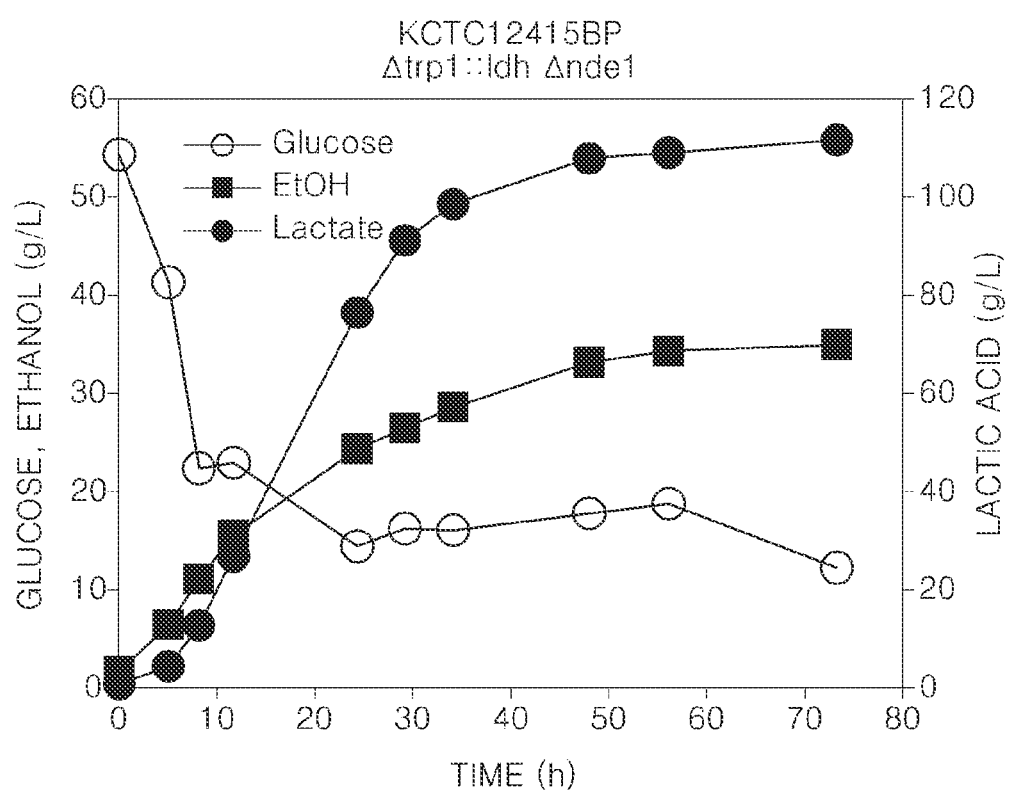
FIG. 8B is a graph illustrating culturing characteristics of a mutant strain of KCTC12415BPΔtrp1::Idh Δ NDE1 under fermentation conditions.
Figure 8C:
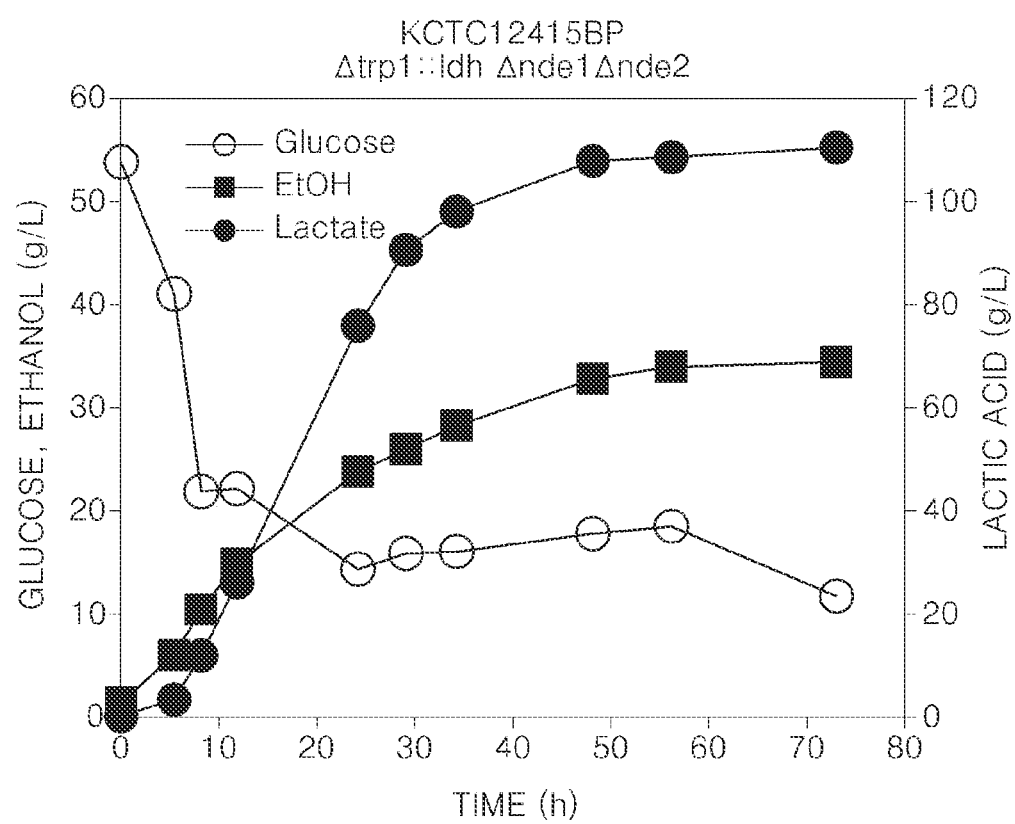
FIG. 8C is a graph illustrating culturing characteristics of a mutant strain of KCTC12415BPΔtrp1::Idh Δ NDE1 Δ NDE2 under fermentation conditions.

FIGS. 8A, 8B, and 8C are each a graph illustrating culturing characteristics of KCTC12415BPΔtrp1::Idh, a mutant strain of KCTC12415BPΔtrp1:Idh Δ nde1, and KCTC12415BP Δ trp1::Idh Δ nde1Δnde2 under fermentation conditions.

[Accession Number]

Research Center Name: Korean Collection for Type Cultures (KTCT)

Accession Number: KCTC 12415BP

Accession Date: May 30, 2013

As described above, according to the one or more of the above embodiments of the present invention, a yeast cell may produce lactate at a high yield. Also, according to the one or more of the above embodiments of the present invention, a method of producing lactate may produce lactate at a high yield.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered yeast cell in which the activity of a protein having a sequence identity of about 95% or more to an external mitochondrial NADH dehydrogenase of SEQ ID NO: 1 or 2 is decreased compared to a parent cell of the genetically engineered yeast cell, wherein
the genetically engineered yeast cell produces lactate,
a gene encoding the external mitochondrial NADH dehydrogenase is inactivated or deleted in the genetically engineered yeast cell,
and the yeast cell comprises a heterologous gene encoding a polypeptide that converts pyruvate to lactate, such that the activity of the polypeptide that converts pyruvate to lactate in the genetically engineered yeast cell is increased as compared to the parent cell.

2. The genetically engineered yeast cell of claim 1, wherein the yeast cell is a *Saccharomyces* genus yeast cell.

3. The genetically engineered yeast cell of claim 1, wherein the external mitochondrial NADH dehydrogenase belongs to EC.1.6.5.9 or EC.1.6.5.3.

4. The genetically engineered yeast cell of claim 1, wherein the external mitochondrial NADH dehydrogenase is NDE1, NDE2, or a combination thereof.

5. The genetically engineered yeast cell of claim 1, wherein the gene encoding the external mitochondrial NADH dehydrogenase has a sequence identity of about 95% or more to a nucleotide sequence of SEQ ID NO: 3 or 4.

6. The genetically engineered yeast cell of claim 1, wherein activity of a polypeptide that converts pyruvate to acetaldehyde, a polypeptide that converts lactate to pyruvate, a polypeptide that converts dihydroxyacetone phosphate (DHAP) to glycerol-3-phosphate, or a combination thereof, in the genetically engineered yeast cell is decreased as compared to a parent cell of the genetically engineered yeast cell, wherein the polypeptide that converts pyruvate to acetaldehyde, the polypeptide that converts lactate to pyruvate, and the polypeptide that converts DHAP to glycerol-3-phosphate each have a sequence identity of about 95% or more to SEQ ID NO: 5, 6, and 7, respectively.

7. The genetically engineered yeast cell of claim 6, wherein the activity of the polypeptide that converts pyruvate to acetaldehyde, the polypeptide that converts lactate to pyruvate, or the polypeptide that converts DHAP to glycerol-3-phosphate, is decreased due to inactivation or deletion of a gene that encodes the polypeptide, wherein the gene that encodes the polypeptide that converts pyruvate to acetaldehyde, the gene that encodes the polypeptide that converts lactate to pyruvate, and the gene that encodes the polypeptide that converts DHAP to glycerol-3-phosphate, each has a sequence identity of about 95% or more to SEQ ID NO: 8, 9, and 10, respectively.

8. The genetically engineered yeast cell of claim 1, wherein activity of a polypeptide that converts pyruvate to lactate is increased by increased expression of a gene encoding the polypeptide that converts pyruvate to lactate in the genetically engineered yeast cell as compared to the parent cell.

9. The genetically engineered yeast cell of claim 8, wherein the polypeptide converting pyruvate to lactate has a sequence identity of about 95% or more to an amino acid sequence of SEQ ID NO: 11.

10. The genetically engineered yeast cell of claim 9, wherein the gene encoding the polypeptide that converts pyruvate to lactate has a sequence identity of about 95% or more to a nucleotide sequence of SEQ ID NO: 15.

11. A method of producing lactate, the method comprises:
culturing the genetically engineered yeast cell of claim 1, whereby the yeast produces lactate; and
collecting lactate from the culture.

12. The method of claim 11, wherein the genetically engineered yeast cell of claim 1 is cultured under anaerobic conditions.

13. A method of providing a genetically engineered yeast cell of claim 1, the method comprising
inactivating the expression of an external mitochondrial NADH dehydrogenase in the yeast, wherein the external mitochondrial NADH dehydrogenase has a sequence identity of about 95% or more to SEQ ID NO: 1 or 2; and
introducing to the yeast cell a heterologous gene encoding a polypeptide that converts pyruvate to lactate so as to produce a polypeptide that converts pyruvate to lactate.

14. The method of claim 13, wherein the expression of the external mitochondrial NADH dehydrogenase is inactivated by mutation or deletion of a gene encoding the external mitochondrial NADH dehydrogenase.

* * * * *